(12) United States Patent
Semizarov et al.

(10) Patent No.: US 9,002,653 B2
(45) Date of Patent: *Apr. 7, 2015

(54) METHODS FOR ASSEMBLING PANELS OF CANCER CELL LINES FOR USE IN TESTING THE EFFICACY OF ONE OR MORE PHARMACEUTICAL COMPOSITIONS

(75) Inventors: Dimitri Semizarov, Chicago, IL (US); Xin Lu, Libertyville, IL (US); Ke Zhang, Glenview, IL (US); Rick R. Lesniewski, Pleasant Prairie, WI (US)

(73) Assignee: AbbVie, Inc., North Chicago, IL (US)

( * ) Notice: Subject to any disclaimer, the term of this patent is extended or adjusted under 35 U.S.C. 154(b) by 672 days.

This patent is subject to a terminal disclaimer.

(21) Appl. No.: 12/607,077

(22) Filed: Oct. 28, 2009

(65) Prior Publication Data

US 2010/0144554 A1   Jun. 10, 2010

Related U.S. Application Data

(60) Provisional application No. 61/110,281, filed on Oct. 31, 2008.

(51) Int. Cl.
| | | |
|---|---|---|
| G01N 33/48 | (2006.01) | |
| G01N 33/50 | (2006.01) | |
| G01N 31/00 | (2006.01) | |
| G06F 19/24 | (2011.01) | |
| G06F 19/12 | (2011.01) | |
| G06F 19/00 | (2011.01) | |
| G06F 17/15 | (2006.01) | |
| G06F 17/17 | (2006.01) | |
| G06F 17/16 | (2006.01) | |
| G06F 17/11 | (2006.01) | |
| G06F 17/10 | (2006.01) | |
| G06F 19/18 | (2011.01) | |

(52) U.S. Cl.
CPC ............ *G06F 19/24* (2013.01); *G06F 19/12* (2013.01); *G06F 19/3443* (2013.01); *G06F 17/15* (2013.01); *G06F 17/17* (2013.01); *G06F 17/16* (2013.01); *G06F 17/11* (2013.01); *G06F 19/3437* (2013.01); *G06F 17/10* (2013.01); *G06F 19/18* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,889,818 A | 12/1989 | Gelfand et al. |
| 5,143,854 A | 9/1992 | Pirrung et al. |
| 5,270,184 A | 12/1993 | Walker et al. |
| 5,310,652 A | 5/1994 | Gelfand et al. |
| 5,322,770 A | 6/1994 | Gelfand |
| 5,384,261 A | 1/1995 | Winkler et al. |
| 5,424,186 A | 6/1995 | Fodor et al. |
| 5,445,934 A | 8/1995 | Fodor et al. |
| 5,455,166 A | 10/1995 | Walker |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,800,992 A | 9/1998 | Fodor et al. |
| 5,856,174 A | 1/1999 | Lipshutz et al. |
| 5,922,591 A | 7/1999 | Anderson et al. |
| 5,998,151 A | 12/1999 | Johnston et al. |
| 6,040,193 A | 3/2000 | Winkler et al. |
| 2005/0209785 A1 | 9/2005 | Wells et al. |
| 2006/0195266 A1 | 8/2006 | Yeatman |

OTHER PUBLICATIONS

Olejniczak et al. Molecular Cancer Research, Apr. 2007, vol. 5, pp. 331-339.*
Anderson et al. Introduction to Statistics, Second Edition. New York: West Publishing Company, 1991, pp. 486-495.*
Craig et al. Proceedings of the Sixth Intervational Conferscence on Information Visualisation, 2002, 7 pages.*
Miozzi et al. PLoS ONE, Jun. 2008, vol. 3, e2439, 7 pages.*
Wolberg et al. Archives of Surgery, 1995, vol. 130, pp. 511-516.*
Devarajan K., "Nonnegative Matrix Factorization: An Analytical and Interpretive Tool in Computational Biology," PLoS Computational Biology, 2008, vol. 4 (7), pp. e1000029.
Gao Y., et al., "Improving Molecular Cancer Class Discovery Through Sparse Non-Negative Matrix Factorization," Bioinformatics, 2005, vol. 21 (21), pp. 3970-3975.
International Search Report and Written Opinion for Application No. PCT/US2009/062421, mailed on Oct. 21, 2010, 15 pages.
Kim H., et al., "Sparse Non-Negative Matrix Factorizations via Alternating Non-Negativity-Constrained Least Squares for Microarray Data Analysis," Bioinformatics, 2007, vol. 23 (12), pp. 1495-1502.
Lu X., et al., "Predicting Features of Breast Cancer With Gene Expression Patterns," Breast Cancer Research Treatment, 2008, vol. 108 (2), pp. 191-201.
Myllykangas S., et al., "Classification of Human Cancers Based on DNA Copy Number Amplification Modeling," BMC Medical Genomics, 2008, vol. 1, pp. 15.
Pascual-Montano A., et al., "BioNMF: A Versatile Tool for Non-Negative Matrix Factorization in Biology," BMC Bioinformatics, 2006, vol. 7, pp. 366.
Wang G., et al., "LS-NMF: A Modified Non-Negative Matrix Factorization Algorithm Utilizing Uncertainty Estimates," BMC Bioinformatics, 2006, vol. 7, pp. 175.
Ausubel F.M., et al., eds., Current Protocols in Molecular Biology, John Wiley & Sons Inc., 2004, Table of Contents.
Bayer E.A., et al., Methods and Biochemical Analysis, 1980, vol. 26, pp. 1-45.

(Continued)

*Primary Examiner* — Russell S Negin
(74) *Attorney, Agent, or Firm* — Changxia Sun

(57) ABSTRACT

The present invention relates to algorithms for use in defining genomic subgroups of tumors and cancer cell lines. The present invention also relates to methods for assembling panels of tumors and cancer cell lines according to genomic subgroups for use in testing the efficacy of one or more pharmaceutical compounds in the treatment of subjects suffering from at least one cancer.

5 Claims, 11 Drawing Sheets

(56) References Cited

OTHER PUBLICATIONS

Bhattacharjee A., et al., "Classification of Human Lung Carcinomas by mRNA Expression Profiling Reveals Distinct Adenocarcinoma Subclasses," Proceedings of the National Academy of Sciences, 2001, vol. 98 (24), pp. 13790-13795.

Borg I., et al., "Modern Multidimensional Scaling" in: Springer Series in Statistics Theory and Applications, 2nd Edition, Springer Verlag, 2005, Table of Contents.

Breiman L., "Random Forests," Machine Learning, 2001, vol. 45, pp. 5-32.

Brigati D.J., et al., "Detection of Viral Genomes in Cultured Cells and Paraffin-Embedded Tissue Sections Using Biotin-Labeled Hybridization Probes," Virology, 1983, vol. 126 (1), pp. 32-50.

Broker T.R., et al., "Electron Microscopic Visualization of tRNA Genes with Ferritin-avidin: Biotin Labels," Nucleic Acids Research, 1978, vol. 5 (2), pp. 363-384.

Brunet J.P., et al., "Metagenes and Molecular Pattern Discovery Using Matrix Factorization," Proceedings of the National Academy of Sciences, 2004, vol. 101 (12), pp. 4164-4169.

Carrasco D.R., et al., "High-Resolution Genomic Profiles Define Distinct Clinicopathogenetic Subgroups of Multiple Myeloma Patients," Cancer Cell, 2006, vol. 9 (4), pp. 313-325.

Connolly B.A., et al., "Chemical Synthesis of Oligonucleotides Containing a Free Sulphydryl Group and Subsequent Attachment of Thiol Specific Probes," Nucleic Acids Research, 1985, vol. 13 (12), pp. 4485-4502.

Efron B., et al., "Least Angle Regression," The Annals of Statistics, 2004, vol. 32 (2), pp. 407-499.

Fodor S.P., et al., "Light-Directed, Spatially Addressable Parallel Chemical Synthesis," Science, 1991, vol. 251 (4995), pp. 767-773.

Fridlyand J., et al., "Hidden Markov Models Approach to the Analysis of Array CGH Data," Journal of Multivariate Analysis, 2004, vol. 90, pp. 132-153.

GeneChip_100KAssayManual_2004_128.
GeneChip_100KAssayManual_2004_129.
GeneChip_100KAssayManual_2004_30.
GeneChip_100KAssayManual_2004_33.
GeneChip_100KAssayManual_2004_36.
GeneChip_100KAssayManual_2004_42.
GeneChip_100KAssayManual_2004_45.
GeneChip_100KAssayManual_2004_49.
GeneChip_100KAssayManual_2004_51.
GeneChip_100KAssayManual_2004_57.
GeneChip_100KAssayManual_2004_93.
GeneChip_500KAssayManual_2005_253.
GeneChip_500KAssayManual_2005_289.
GeneChip_500KAssayManual_2005_292.
GeneChip_500KAssayManual_2005_74.
GeneChip® Mapping 500K Assay Manual, 2005 Table of Contents only.

Hedenfalk I., et al., "Molecular Classification of Familial Non-BRCA1/BRCA2 Breast Cancer," Proceedings of the National Academy of Sciences, 2003, vol. 100 (5), pp. 2532-2537.

Hodgson G., et al., "Genome Scanning with Array CGH Delineates Regional Alterations in Mouse Islet Carcinomas," Nature Genetics, 2001, vol. 29 (4), pp. 459-464.

Holland P.M., et al., "Detection of Specific Polymerase Chain Reaction Product by Utilizing the 5'→3' Exonuclease Activity of Thermus Aquaticus DNA Polymerase," Proceedings of the National Academy of Sciences, 1991, vol. 88 (16), pp. 7276-7280.

Hopman A.H.N., et al., "Mercurated Nucleic Acid Probes, A New Principle for Non-Radioactive In Situ Hybridization", Experimental Cell Research, 1987, vol. 169, pp. 357-368.

Hupe P., et al., "Analysis of Array CGH Data: From Signal Ratio to Gain and Loss of DNA Regions," Bioinformatics, 2004, vol. 20 (18), pp. 3413-3422.

Innis M.A., et al., eds., "A Guide to Methods and Applications", in: PCR Protocols, Academic Press Inc., 1990, Table of Contents.

Innis M.A., et al., eds., PCR Strategies, Academic Press Inc., 1995, Table of Contents.

Joos S., et al., "Mapping and Chromosome Analysis: the Potential of Fluorescence in Situ Hybridization," Journal of Biotechnology, 1994, vol. 35, pp. 135-153.

Kricka L.J., et al., "Stains, Labels and Detection Strategies for Nucleic Acids Assays," Ann. Clin. Biochem., 2002, vol. 39, pp. 114-129.

Landegent J.E., et al., "2-Acetylaminofluorene-modified Probes for the Indirect Hybridocytochemical Detection of Specific Nucleic Acid Sequences", Experimental Cell Research, 1984, vol. 153, pp. 61-72.

Langer P., et al., "Enzymatic Synthesis of Biotin-labeled Polynucleotides: Novel Nucleic Acid Affinity Probes," in Proc. Natl. Acad. Sci., 1981, vol. 78 (11), pp. 6633-6637.

Lee D.D., et al., "Learning the Parts of Objects by Non-Negative Matrix Factorization," Nature, 1999, vol. 401 (6755), pp. 788-791.

Li C., et al., "Model-based Analysis of Oligonucleotide Arrays: Expression Index Computation and Outlier Detection," Proceedings of the National Academy of Sciences, 2001, vol. 98 (1), pp. 31-36.

Li C., et al., "Model-based Analysis of Oligonucleotide Arrays: Model Validation Design Issues and Standard Error Application," Genome Biology, 2001, vol. 2 (8), RESEARCH0032.

Lin W.M., et al., "Modeling Genomic Diversity and Tumor Dependency in Malignant Melanoma," Cancer Research, 2008, vol. 68 (3), pp. 664-673.

Maher E.A., et al., "Marked Genomic Differences Characterize Primary and Secondary Glioblastoma Subtypes and Identify Two Distinct Molecular and Clinical Secondary Glioblastoma Entities," Cancer Research, 2006, vol. 66 (23), pp. 11502-11513.

Matsuzaki H., et al., "Genotyping Over 100,000 SNPs on a Pair of Oligonucleotide Arrays," Nature Methods, 2004, vol. 1 (2), pp. 109-111.

McPherson M.J., et al., eds., PCR: A Practical Approach, Oxford University Press, 1991, Table of Contents.

Olshen A.B., et al., "Circular Binary Segmentation for the Analysis of Array-based DNA Copy Number Data," Biostatistics, 2004, vol. 5 (4), pp. 557-572.

Pearson K., et al., "On Lines and Planes of Closest Fit to Systems of Points in Space," Philosophical Magazine, 1901, vol. 2 (11), pp. 559-572.

Reich M., et al., "GenePattern 2.0," Nature Genetics, 2006, vol. 38 (5), pp. 500-501.

Richardson R W., et al., "Biotin and Fluorescent Labeling of RNA Using T4 RNA Ligase," Nucleic Acids Research, 1983, vol. 11 (18), pp. 6167-6184.

Ross D.T., et al., "Systematic Variation in Gene Expression Patterns in Human Cancer Cell Lines," Nature Genetics, 2000, vol. 24 (3), pp. 227-235.

Saiki R.K., et al., "Analysis of Enzymatically Amplified β-Globin and HLA-DQ α DNA with Allele-Specific Oligonucleotide Probes," Nature, 1986, vol. 324 (6093), pp. 163-166.

Sambrook J., et al., eds., Molecular Cloning: A Laboratory Manual, 3rd Edition, Cold Spring Harbor Laboratory, 2001, Table of Contents.

Schwarz G., "Estimating the Dimension of a Model," Annals of Statistics, 1978, vol. 6 (2), pp. 461-464.

Smith L M., et al., "The Synthesis of Oligonucleotides Containing an Aliphatic Amino Group at the 5' Terminus: Synthesis of Fluorescent DNA Primers for use in DNA Sequence Analysis," Nucleic Acids Research, 1985, vol. 13 (7), pp. 2399-2412.

Sotiriou C., et al., "Breast Cancer Classification and Prognosis Based on Gene Expression Profiles from a Population-based Study," Proceedings of the National Academy of Sciences, 2003, vol. 100 (18), pp. 10393-10398.

Tchen P., et al., "Chemically Modified Nucleic Acids as Immunodetectable Probes in Hybridization Experiments", Proceedings of the National Academy of Sciences, 1984, vol. 81, pp. 3466-3470.

Temsamani J. et al., "Enzymatic Labeling of Nucleic Acids," Molecular Biotechnology, 1996, vol. 5 (3), pp. 223-232.

Van Gijlswijk R PM., et al., "Universal Linkage System Versatile Nucleic Acid Labeling Technique," Expert Rev. Mol. Diagn., 2001, vol. 1 (1), pp. 81-91.

Vapnik V.N., "The Nature of Statistical Learning Theory," Springer Verlag, 1995, Table of Contents.

(56) References Cited

OTHER PUBLICATIONS

Vogel C.L., et al., "Efficacy and Safety of Trastuzumab as a Single Agent in First-Line Treatment of HER2-Overexpressing Metastatic Breast Cancer," Journal of Clinical Oncology, 2002, vol. 20 (3), pp. 719-726.

Wang P., et al., "A Method for Calling Gains and Losses in Array CGH Data," Biostatistics, 2005, vol. 6 (1), pp. 45-58.

Wilhelm M., et al., "Array-based Comparative Genomic Hybridization for the Differential Diagnosis of Renal Cell Cancer," Cancer Research, 2002, vol. 62 (4), pp. 957-960.

Zhang X., et al., "Recursive SVM Feature Selection and Sample Classification for Mass-spectrometry and Microarray Data," BMC Bioinformatics, 2006, vol. 7, pp. 197.

Zhao X., et al., "An Integrated View of Copy Number and Allelic Alterations in the Cancer Genome Using Single Nucleotide Polymorphism Arrays," Cancer Research, 2004, vol. 64 (9), pp. 3060-3071.

Anand S., et al., "AURORA-A Amplification Overrides the Mitotic Spindle Assembly Checkpoint, Inducing Resistance to Taxol," Cancer Cell, 2003, vol. 3 (1), pp. 51-62.

Fearon E.R., et al., "A Genetic Model for Colorectal Tumorigenesis," Cell, 1990, vol. 61 (5), pp. 759-767.

Greshock J., et al., "A Comparison of DNA Copy Number Profiling Platforms," Cancer Research, 2007, vol. 67 (21), pp. 10173-10180.

Hirsch F.R., et al., "Molecular Predictors of Outcome With Gefitinib in a Phase III Placebo-Controlled Study in Advanced Non-Small-Cell Lung Cancer," Journal of Clinical Oncology, 2006, vol. 24 (31), pp. 5034-5042.

Innis M.A., et al., eds., "Protocols for Functional Genomics" in: PCR Applications, Academic Press Inc., 1999, Table of Contents.

International Preliminary Report on Patentability and Written Opinion for Application No. PCT/US2009/062411, mailed on May 3, 2011, 7 pages.

International Preliminary Report on Patentability and Written Opinion for Application No. PCT/US2009/062414, mailed on May 3, 2011, 7 pages.

Lee D.D., et al., "Algorithms for Non-Negative Matrix Factorization," Advances in Neural Information Processing Systems, 2000, vol. 13, pp. 556.

Levsky J.M., et al., "Fluorescence in Situ Hybridization: Past, Present and Future," Journal of Cell Science, 2003, vol. 116 (Pt 14), pp. 2833-2838.

Midgley R., et al., "Colorectal Cancer," Lancet, 1999, vol. 353 (9150), pp. 391-399.

Onken M.D., et al., "Gene Expression Profiling in Uveal Melanoma Reveals Two Molecular Classes and Predicts Metastatic Death," Cancer Research, 2004, vol. 64 (20), pp. 7205-7209.

Ried T., et al., "Comparative Genomic Hybridization Reveals a Specific Pattern of Chromosomal Gains and Losses During the Genesis of Colorectal Tumors," Genes, Chromosomes & Cancer, 1996, vol. 15 (4), pp. 234-245.

Seeger R.C., et al., "Association of Multiple Copies of the N-myc Oncoge with Rapid Progression of Neuroblastomas," The New England Journal of Medicine, 1985, vol. 313 (18), pp. 1111-1116.

Song J.H., et al., "Cisplatin Down-Regulation of Cellular Fas-Associated Death Domain-Like Interleukin-1beta-Converting Enzyme-Like Inhibitory Proteins to Restore Tumor Necrosis Factor-Related Apoptosis-Inducing Ligand-Induced Apoptosis in Human Melanoma Cells," Clinical Cancer Research, 2003, vol. 9 (11), pp. 4255-4266.

Su A.L., et al., "Molecular Classification of Human Carcinomas by Use of Gene Expression Signatures", Cancer Research, 2001, vol. 61 (20), pp. 7388-7393.

Tucker M.A., et al., "Melanoma Etiology: Where Are We," Oncogene, 2003, vol. 22 (20), pp. 3042-3052.

Weyers W., et al., "Classification of Cutaneous Malignant Melanoma a Reassessment of Histopathologic Criteria for the Distinction of Different Types," Cancer, 1999, vol. 86 (2), pp. 288-299.

\* cited by examiner (a)

(b)

SEQUENCE LISTING

<160> NUMBER OF SEQ ID NOS: 8

<210> SEQ ID NO 1
<211> LENGTH: 27
<212> TYPE: DNA
<213> ORGANISM: Artificial sequence
<220> FEATURE:
<223> OTHER INFORMATION: Chemical Synthesized

<400> SEQUENCE: 1
attatgagca cgacagacgc ctgatct                                  27

<210> SEQ ID NO 2
<211> LENGTH: 31
<212> TYPE: DNA
<213> ORGANISM: Artificial Sequence
<220> FEATURE:
<223> OTHER INFORMATION: Chemically synthesized

<400> SEQUENCE: 2
tctagagatc aggcgtctgt cgtgctcata a                             31

<210> SEQ ID NO 3
<211> LENGTH: 30
<212> TYPE: DNA
<213> ORGANISM: Artificial Sequence
<220> FEATURE:
<223> OTHER INFORMATION: Chemically synthesized

<400> SEQUENCE: 3
acgtagatca ggcgtctgtc gtgctcataa                               30

<210> SEQ ID NO 4
<211> LENGTH: 27
<212> TYPE: DNA
<213> ORGANISM: Artificial Sequence
<220> FEATURE:
<223> OTHER INFORMATION: Chemically synthesized

<400> SEQUENCE: 4
attatgagca cgacagacgc ctgatct                                  27

<210> SEQ ID NO 5
<211> LENGTH: 31
<212> TYPE: DNA
<213> ORGANISM: Artificial Sequence
<220> FEATURE:
<223> OTHER INFORMATION: Chemically synthesized

<400> SEQUENCE: 5
attatgagca cgacagacgc ctgatctcat g                             31

<210> SEQ ID NO 6
<211> LENGTH: 26
<212> TYPE: DNA
<213> ORGANISM: Artificial Sequence
<220> FEATURE:
<223> OTHER INFORMATION: Chemically synthesized

<400> SEQUENCE: 6
agatcaggcg tctgtcgtgc tcataa                                   26

<210> SEQ ID NO 7
<211> LENGTH: 27
<212> TYPE: DNA
<213> ORGANISM: Artificial Sequence

```
<220> FEATURE:
<223> OTHER INFORMATION: Chemically synthesized

<400> SEQUENCE: 7
attatgagca cgacagacgc ctgatct                                              27

<210> SEQ ID NO 8
<211> LENGTH: 30
<212> TYPE: DNA
<213> ORGANISM: Artificial sequence
<220> FEATURE:
<223> OTHER INFORMATION: Chemically synthesized
<220> FEATURE:
<221> NAME/KEY: misc_feature
<222> LOCATION: (2)..(3)
<223> OTHER INFORMATION: w= a or t/u

<400> SEQUENCE: 8
cwwgagatca ggcgtctgtc gtgctcataa                                           30
```

METHODS FOR ASSEMBLING PANELS OF CANCER CELL LINES FOR USE IN TESTING THE EFFICACY OF ONE OR MORE PHARMACEUTICAL COMPOSITIONS

RELATED APPLICATION INFORMATION

This application claims priority to U.S. Application No. 61/110,281 filed on Oct. 31, 2008, the contents of which are herein incorporated by reference.

SEQUENCE LISTING

The instant application contains a Sequence Listing which has been submitted via EFS-Web and is hereby incorporated by reference in its entirety. Said ASCII copy is named 9674USO1.txt and is 1.8 kilobytes in size.

FIELD

The present invention relates to bioinformatics algorithms or methods for use in defining genomic subgroups of tumors and cancer cell lines. The present invention also relates to methods for assembling panels of tumors and cancer cell lines according to genomic subgroups for use in testing the efficacy of one or more pharmaceutical compounds in the treatment of subjects suffering from at least one cancer.

BACKGROUND

Cancer is a disease of the genome characterized by substantial variability in clinical course, outcome, and response to therapies. The main factor underlying this variability is the genetic heterogeneity of human cancers. It has been demonstrated that individual tumors of the same histopathological subtype carry different aberrations in their cellular DNA. It is recognized that targeted cancer therapies target specific genetic aberrations rather than histological disease subtypes. Some examples of drugs that target molecular abnormalities are imatinib mesylate (which is used to treat chronic myelogenous leukemia) and trastuzumab (which is used to treat HER2-positive breast cancer).

Currently, pre-clinical models for oncology drug testing are selected based on their availability, adaptability to tumor formation in mice, growth in culture, as well as other parameters. The problem with this approach is that it does not take into account the genetic heterogeneity of the parent tumor. This results in a poor representation of molecular subtypes of tumors during preclinical testing. Thus, the high response rates that are frequently seen in preclinical testing may only represent the response of the molecular subtype represented in the preclinical testing laboratory. If this subtype represents only a fraction of the patient population, and if the drug is efficacious only against this specific subtype, then the response in the clinic will be significantly lower. Therefore, there is a need in the art for improved pre-clinical testing models that better represent all parent tumor types. Such improved pre-clinical testing will increase the predictability of the preclinical testing of new drugs.

SUMMARY OF THE INVENTION

In one aspect, the present invention relates to algorithm for use in clustering tumors and cell lines to define genomic subgroups. The algorithm comprising the steps of:

(a) obtaining a plurality of m samples comprising at least one tumor or cancer cell line;

(b) acquiring a data set comprising copy number alteration information from at least one locus from each chromosome from each sample obtained in step (a);

(c) identifying in the data set, copy number alteration information obtained from samples contaminated by normal cells and eliminating the contaminated samples from the data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the data set for each sample scoring 50% or greater probability of containing normal cells;

(d) estimating a number of subgroups, r, in the data set by applying an unsupervised clustering algorithm using Pearson linear dissimilarity algorithm to the data set;

(e) assigning each sample in the data set to at least one cluster using a modified genomic non-negative matrix factorization (gNMF) algorithm, wherein the modified gNMF algorithm comprises:

(1) calculating divergence of the algorithm after every 100 steps of multiplicative updating using the formula (1):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (1)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

(2) stopping the algorithm if the divergence calculated in step (e) (1) does not decrease by more than about 0.001% when compared to the divergence calculated for the previous 100 steps of multiplicative updating of the algorithm;

(3) randomly repeating the algorithm for a selected number of runs and calculating a Pearson correlation coefficient matrix of H for the each of run the algorithm using the formula (2):

$$C_{i,j} = \rho(H_{\cdot,i}, H_{\cdot,j}) = \frac{\frac{1}{r-1}\sum_{k}(H_{k,i} - \overline{H_{\cdot,i}})(H_{k,j} - \overline{H_{\cdot,j}})}{s_{H_{\cdot,i}}s_{H_{\cdot,j}}} \quad (2)$$

wherein C is the correlation matrix, $C_{i,j}$ is the $i^{th}$ row and $j^{th}$ column in the matrix C, $H_{\cdot,i}$ and $H_{\cdot,j}$ are the $i^{th}$ and $j^{th}$ column vector in matrix H, $\rho(H_{\cdot,i}, H_{\cdot,j})$ is the Pearson correlation coefficient between $H_{\cdot,i}$ and $H_{\cdot,j}$, i and j run from 1 to m and m is the number of samples in the data set, k runs from 1 to r and r is the number of subgroups from step (d);

(4) averaging the Pearson correlation coefficient matrices for each run of the algorithm obtained from step (e)(3) to arrive at an average correlation matrix;

(5) assigning tumors and cancer cell lines in the data set into r subgroups by applying a unsupervised clustering algorithm using 1 minus the average correlation matrix determined in step (e)(4) and cutting a dendrogram into r clusters;

(f) applying a Cophenetic correlation, Bayesian Information Criterion or a combination thereof to provide a final number of clusters from the data set, wherein each final cluster defines a genomic subgroup for each tumor or cancer cell line sample; and (g) evaluating the stability of the final number of clusters selected in step (f) using a ten-fold stability test.

In the above algorithm, the unsupervised clustering algorithm is a hierarchical clustering. Additionally, in the above algorithm, Cophenetic correlation is used to provide a final number of clusters from the data set. Alternatively, in the above algorithm, Bayesian Information Criterion is used to provide a final number of clusters from the data set. Still in another alternative, in the above algorithm, Cophenetic correlation and Bayesian Information Criterion are used to provide a final number of clusters from the data set.

In another aspect, the present invention relates to a method for assembling panels of tumor and cancer cell lines according to genomic subgroups. The method comprises the steps of:

(a) obtaining a plurality of m samples comprising at least one tumor or cancer cell line;

(b) acquiring a data set comprising copy number alteration information from at least one locus from each chromosome from each sample obtained in step (a);

(c) identifying in the data set, copy number alteration information obtained from samples contaminated by normal cells and eliminating the contaminated samples from the data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the data set for each sample scoring 50% or greater probability of containing normal cells;

(d) estimating a number of subgroups, r, in the data set by applying unsupervised clustering using Pearson linear dissimilarity algorithm to the data set;

(e) assigning each sample in the data set to at least one cluster using a modified genomic non-negative matrix factorization (gNMF) algorithm, wherein the modified gNMF algorithm comprises:

(1) calculating divergence of the algorithm after every 100 steps of multiplicative updating using the formula (1):

$$D(V\|WH) = \sum_{i=1}^{n} \sum_{j=1}^{m} \left( V_{ij} \log \frac{V_{ij}}{(WH)_{ij}} - V_{ij} + (WH)_{ij} \right) \quad (1)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

(2) stopping the algorithm if the divergence calculated in step (e) (1) does not decrease by more than about 0.001% when compared to the divergence calculated for the previous 100 steps of multiplicative updating of the algorithm;

(3) randomly repeating the algorithm for a selected number of runs and calculating a Pearson correlation coefficient matrix of H for the each of run the algorithm using the formula (2):

$$C_{i,j} = \rho(H_{,i}, H_{,j}) = \frac{\frac{1}{r-1}\sum_{k}(H_{k,i} - \overline{H_{,i}})(H_{k,j} - \overline{H_{,j}})}{s_{H_{,i}} s_{H_{,j}}} \quad (2)$$

wherein C is the correlation matrix, $C_{i,j}$ is the $i^{th}$ row and $j^{th}$ column in the matrix C, $H_{,i}$ and $H_{,j}$ are the $i^{th}$ and $j^{th}$ column vector in matrix H, $\rho(H_{,i}, H_{,j})$ is the Pearson correlation coefficient between $H_{,i}$ and $H_{,j}$, i and j run from 1 to m and m is the number of samples in the data set, k runs from 1 to r and r is the number of subgroups from step (d);

(4) averaging the Pearson correlation coefficient matrices for each run of the algorithm obtained from step (e)(3) to arrive at an average correlation matrix;

(5) assigning tumors and cancer cell lines in the data set into r subgroups by applying a unsupervised clustering algorithm using 1 minus the average correlation matrix determined in step (e)(4) and cutting a dendrogram into r clusters;

(f) applying a Cophenetic correlation, Bayesian Information Criterion or a combination thereof to select a final number of clusters from the data set;

(g) evaluating the stability of the final number of clusters selected in step (f) using a ten-fold stability test; and (h) selecting at least one tumor or cell line from each cluster selected in step (f) and assembling into panels defined according to genomic subgroups.

In the above method, cancer is selected from the group consisting of: small cell lung carcinoma, non-small cell lung carcinoma, colorectal cancer and melanoma.

In the above method, the copy number alteration is a gain or loss or copy number.

DETAILED DESCRIPTION

Figure 1:
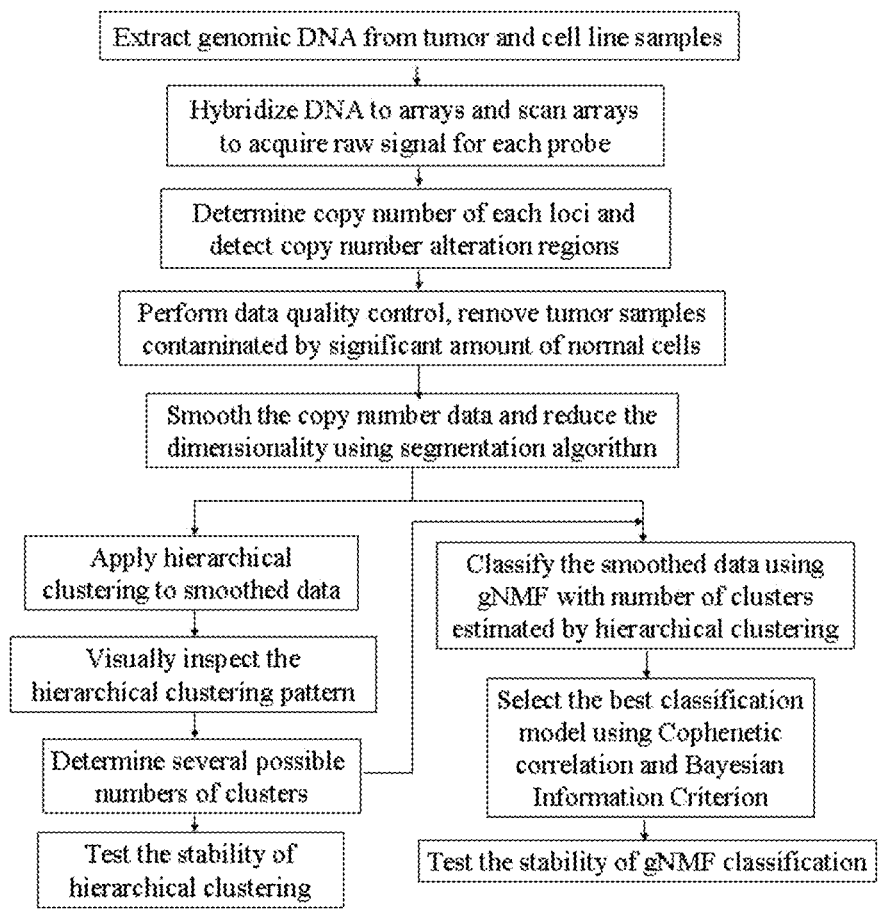
FIG. 1 shows an outline of the steps involved in the methods of present invention. Specifically, this figure shows the steps involved in classifying tumors and cancer cell lines based on their copy number pattern, assigning the tumors and cancer cell lines to genomic subgroups based on their patterns of copy number alterations and then assembling panels of cells to represent the genomic subgroups for a specific cancer type.

In one aspect, the present invention provides a methodology for assembling panels of tumors, cancer cell lines and/or xenografts for pre-clinical testing of pharmaceutical compositions that can be used in treating subjects (e.g. human patients) suffering from at least one type of cancer. Using the methods described herein, panels of cancer cell lines representative of the genomic diversity of a parent tumor type can be developed by selecting cancer cell lines so that each of them match a distinct genomic subgroup of the corresponding tumor type.

In another aspect, the present invention provides a unique computational algorithm that can be used to define or classify genomic subgroups of tumor and cancer cell lines. The genomic subgroups identified from these tumor and cancer cell lines can be used to assemble the panels discussed above. Generally, the computational algorithm of the present invention comprises the following steps:

1. Applying a machine learning algorithm (such as Random Forests) to identify and eliminate samples with significant contamination by normal cells;
2. Using unsupervised clustering (such as hierarchical clustering) to estimate the possible numbers of clusters before fitting the data with a genomic Non-negative Matrix Factorization (gNMF) model;
3. Using multiple random starts of gNMF followed by the application of the correlation of H matrix resulting from gNMF as the distance matrix to classify samples;
4. Classifying tumors and cancer cell lines into several possible numbers of clusters using the gNMF algorithm, followed by the use of the Cophenetic correlation coefficient, Bayesian Information Criterion (BIC) or combinations thereof to select the best model and determine the final number of clusters; and
5. Applying a 10-fold stability test to evaluate the stability of the clusters.

The methods of the present invention facilitate rational selection of preclinical testing models and improve the predictability of preclinical testing by providing a more complete representation of parent tumors. While not wishing to be bound by any theory, the fundamental principle of the present invention is as follows. Patterns of copy number alterations (CNAs) have been shown to determine the phenotypes of human tumors. Thus, if subgroups of tumor populations are defined by patterns of CNAs and then at least one cell line is selected to match each subgroup, a panel of cell lines can be assembled that represents the diversity of the tumor population more adequately than the presently available sets of tumor models.

A. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Array

The term "array" as used herein refers to nucleic acid probes attached to a solid support. Arrays typically comprise a plurality of different nucleic acid probes that are coupled to a surface of a substrate in different, known locations. These arrays, also described as microarrays, "chips" have been generally described in the art, for example, U.S. Pat. Nos. 5,143,854, 5,445,934, 5,744,305, 5,677,195, 6,040,193, 5,424,186 and (See, Fodor, S. P., et al., "Light-directed, spatially addressable parallel chemical synthesis," *Science*, 251:767-773 (1991)). These arrays can generally be produced using mechanical synthesis methods or light directed synthesis methods that incorporate a combination of photolithographic methods and solid phase synthesis methods. Techniques for the synthesis of arrays using mechanical synthesis are described in, e.g., U.S. Pat. No. 5,384,261. Although a planar array surface is preferred, the array can be fabricated on a surface of virtually any shape or even a multiplicity of surfaces. Arrays can be nucleic acids on beads, gels, polymeric surfaces, fibers such as fiber optics, glass or any other appropriate substrate; e.g., as described in U.S. Pat. Nos. 5,770,358, 5,789,162, 5,708,153, 6,040,193 and 5,800,992. Arrays can be packaged in such a manner as to allow for diagnostics or other manipulation of an all inclusive device, see for example, U.S. Pat. Nos. 5,856,174 and 5,922,591.

Arrays can be designed to cover an entire genome using single nucleotide polymorphisms (SNPs). For example, an array can cover 116,204 single-nucleotide polymorphism (SNP) loci in the human genome with a mean inter-marker distance of 23.6 kb SNP loci with a mean inter-marker distance of 23.6 kb loci.

b) Bayesian Information Criterion (BIC)

As used herein, the phrase "Bayesian Information Criterion" or "BIC" refers to a parametric method which is used as a statistical criterion for model selection. BIC was described by Schwarz, G. in "Estimating the dimension of a model", in the *Annals of Statistics* 6(2):461-464 (1978). BIC is defined by the following formula (3):

$$BIC = -2*\ln(L) + k\ln(n) \qquad (3)$$

wherein L is the likelihood which measures how good the model approximates the data, k is the number of parameters used in the model, and n is the number of samples. The second term, kln(n), serves as a penalty on the number of parameters used in the model to avoid overfitting.

c) Clustering Analysis

As used herein, the phrase, "clustering analysis", refers to the grouping of a collection of objects (also called observations, individuals, cases, or data rows) into subsets, subgroups or "clusters", such that those within each cluster are more closely related to one another than objects assigned to different clusters. Central to all of the goals of clustering analysis is the notion of degree of similarity (or dissimilarity) between the individual objects being clustered. Examples of types of clustering are hierarchical clustering and k-means clustering.

d) Cophenetic Correlation Coefficient or Cophenetic Correlation

As used herein, the phrases, "Cophenetic Correlation Coefficient" or "Cophenetic Correlation", as used interchangeably herein, refer to algorithms that are used to measure how faithfully a dendrogram used to derive the final clustering result preserves the pairwise distances between the original unmodeled data points. For use in the present invention, if it is supposed that the original data $X_i$ has been modeled by a dendrogram $T_i$, distance measures are defined by the following formula:

$x(i,j)=|X_i-X_j|$, the distance between the $i^{th}$ and $j^{th}$ samples and t(i,j)=the dendrogrammatic distance between the model points $T_i$ and $T_j$, where the distance is the height of the node at which these two points are first joined together. Then, if x is the average of x(i,j), and t is the average of t(i,j), the Cophenetic correlation coefficient c is defined by the following formula (4):

$$c = \frac{\sum_{i<j}(x(i,j)-x)(t(i,j)-t)}{\sqrt{\left[\sum_{i<j}(x(i,j)-x)^2\right]\left[\sum_{i<j}(t(i,j)-t)^2\right]}} \quad (4)$$

It is known (See, Maher, E. A., et al., "Marked genomic differences characterize primary and secondary glioblastoma subtypes and identify two distinct molecular and clinical secondary glioblastoma entities," *Cancer Res.* 66:11502-13 (2006); Carrasco, D. R., et al., "High-resolution genomic profiles define distinct clinico-pathogenetic subgroups of multiple myeloma patients," *Cancer Cell.* 9:313-25 (2006)) that with the increase of r, the Cophenetic correlation will decrease dramatically at a certain point, thus corresponding to the best number of clusters.

e) Directly Detectable and Indirectly Detectable

As used herein, the phrase, "directly detectable", when used in reference to a detectable label or detectable moiety, means that the detectable label or detectable moiety does not require further reaction or manipulation to be detectable. For example, a fluorescent moiety is directly detectable by fluorescence spectroscopy methods. In contrast, the phrase "indirectly detectable", when used herein in reference to a detectable label or detectable moiety, means that the detectable label or detectable moiety becomes detectable after further reaction or manipulation. For example, a hapten becomes detectable after reaction with an appropriate antibody attached to a reporter, such as a fluorescent dye.

f) Hierarchical Clustering

As used herein, the phrase, "hierarchical clustering" refers to the building (agglomerative), or break up (divisive), of a hierarchy of clusters. The traditional representation of this hierarchy is a tree (which is referred to as dendrogram), with individual elements at one end and a single cluster containing every element at the other. Agglomerative algorithms begin at the leaves of the tree, whereas divisive algorithms begin at the root. Methods for performing hierarchical clustering are well known in the art.

Hierarchical clustering method has been widely used to cluster biological samples based on their genomic patterns and derive subgroup structures in populations of samples in biomedical research (See, Sotiriou, C et al., "Breast cancer classification and prognosis based on gene expression profiles form a population-based study," *Proc. Natl. Acad. Sci. USA*, 100:10393-10398 (2003); Bhattacharjee, A., et al., "Classification of human lung carcinomas by mRNA expression profiling reveals distinct adenocarcinoma subclasses," *Proc. Natl. Acad. Sci. USA*, 98:13790-13795 (2001); Wilhelm, M., "Array-based Comparative Genomic Hybridization for the Differential Diagnosis of Renal Cell Cancer," *Cancer Research* 62:957-960 (Feb. 15, 2002); Hedenfalk, I., et al., "Molecular classification of familial non-BRCA1/BRCA2 breast cancer," *Proc. Natl. Acad. Sci. USA*, 100: 2532-2537 (2003)). For example, in Ross, D. T., et al. (See, Ross, D. T., et al., "Systematic variation in gene expression patterns in human cancer cell lines," *Nat. Genet.*, 24:227-235 (2000)) hierarchical clustering was used to group 64 human tumor cell lines into several clusters based on the expression pattern of 1161 selected genes, and derive the molecular signatures of different clusters.

g) Hybridization

As used herein, the term "hybridization" refers to the formation of complexes between nucleic acid sequences, which are sufficiently complementary to form complexes via Watson-Crick base pairing or non-canonical base pairing. For example, when a primer "hybridizes" with a target sequence (template), such complexes (or hybrids) are sufficiently stable to serve the priming function required by, e.g., the DNA polymerase, to initiate DNA synthesis. It will be appreciated by one skilled in the art that hybridizing sequences need not have perfect complementarity to provide stable hybrids. In many situations, stable hybrids will form where fewer than about 10% of the bases are mismatches. Accordingly, as used herein, the term "complementary" refers to an oligonucleotide that forms a stable duplex with its complement under assay conditions, generally where there is about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater homology. Those skilled in the art understand how to estimate and adjust the stringency of hybridization conditions such that sequences having at least a desired level of complementarity will stably hybridize, while those having lower complementarity will not. Examples of hybridization conditions and parameters can be found, for example in, Sambrook et al., "*Molecular Cloning: A Laboratory Manual*", 1989, Second Edition, Cold Spring Harbor Press: Plainview, N.Y.; F. M. Ausubel, "*Current Protocols in Molecular Biology*", 1994, John Wiley & Sons: Secaucus, N.J.

h) Labeled or Labeled with a Detectable Label

As used herein, the terms "labeled" and "labeled with a detectable label (or agent or moiety)" are used interchangeably herein and specify that an entity (e.g., a fragment of DNA, a primer or a probe) can be visualized, for example following binding to another entity (e.g., an amplification product). Preferably, the detectable label is selected such that it generates a signal which can be measured and whose intensity is related to (e.g., proportional to) the amount of bound entity. A wide variety of systems for labelling and/or detecting nucleic acid molecules, such as primer and probes, are well-known in the art. Labeled nucleic acids can be prepared by incorporation of, or conjugation to, a label that is directly or indirectly detectable by spectroscopic, photochemical, biochemical, immunochemical, electrical, optical, chemical or other means. Suitable detectable agents include, but are not limited to, radionuclides, fluorophores, chemiluminescent agents, microparticles, enzymes, colorimetric labels, magnetic labels, haptens and the like.

i) Machine Learning

As used herein, the phrase "machine learning" refers to a subfield of artificial intelligence that relates to the design and development of algorithms and techniques that allows computers to "learn". In general, there are two types of learning: inductive, and deductive. Inductive machine learning methods extract rules and patterns out of data sets. The major focus of machine learning research is to extract information from data automatically, by computational and statistical methods. A number of machine learning algorithms, which are organized into a taxonomy, based on the desired outcome of the algorithm, are known to those skilled in the art. These include, but are not limited to: (1) supervised learning (e.g., Random Forests); (2) unsupervised learning (e.g., principal components analysis, vector quantization, etc.); (3) semi-supervised learning; (4) reinforcement learning; (5) transduction; and (6) learning to learn.

j) Non-Negative Matrix Factorization

As used herein, the phrase "Non-Negative Matrix Factorization" or "NMF" refers to an algorithm for finding parts-based, linear representations of non-negative data. Non-Negative Matrix Factorization was originally developed as a mathematical tool for use in image analysis (See, Lee, D. D., et al., "Learning the parts of objects by non-negative matrix factorization," *Nature*. 401:788-91 (1999); Lee, D. D. et al., "Algorithms for Non-negative Matrix Factorization," *Advances In Neural Information Processing Systems*. 14:556-562 (2001)).

NMF was adopted in genomics for analysis of gene expression data (See, Brunet, J. P., et al., Metagenes and molecular pattern discovery using matrix factorization. *Proc Natl Acad Sci USA*. 101:4164-9 (2004)). Specifically, NMF was adapted for use in the analysis of gene copy number data (See, Maher, E. A., et al., "Marked genomic differences characterize primary and secondary glioblastoma subtypes and identify two distinct molecular and clinical secondary glioblastoma entities," *Cancer Res*. 66:11502-13 (2006); Carrasco, D. R., et al., "High-resolution genomic profiles define distinct clinicopathogenetic subgroups of multiple myeloma patients," *Cancer Cell*. 9:313-25 (2006)). The variation of the method used for gene copy number analysis is referred to as genomic Non-negative Matrix Factorization (gNMF). Given a n×m matrix V of smoothed copy number data in the data set, where n is the number of segments and m is the number of samples, the gNMF algorithm factorizes the matrix V into an n×r matrix W and a r×m matrix H as shown in the below formula (5):

$$V = W*H + e \tag{5}$$

In the present invention, W can be viewed as the standard model for each subgroup; H as relative weights of each sample belonging to each subgroup; e represents the model fitting residues, and r is the number of subgroups to be clustered (which is usually much smaller than m). Given r and V as inputs, the gNMF algorithm first randomly sets the initial value of W and H, and then iteratively updates W and H using multiplicative update rules pursuant to the below formulas (6 and 7):

$$H_{a\mu} \leftarrow H_{a\mu} \frac{\sum_i W_{ia} V_{i\mu} / (WH)_{i\mu}}{\sum_k W_{ka}} \tag{6}$$

$$W_{ia} \leftarrow W_{ia} \frac{\sum_\mu H_{a\mu} V_{i\mu} / (WH)_{i\mu}}{\sum_v H_{av}} \tag{7}$$

wherein α runs from 1 to r, μ runs from 1 to m, and i runs from 1 to n.

k) Pearson Linear Dissimilarity

As used herein, the phrase, "Pearson linear dissimilarity" refers to the below formula (8):

$$d_\rho(\vec{x}, \vec{y}) = \frac{1 - \rho(\vec{x}, \vec{y})}{2} \tag{8}$$

wherein $\vec{x}$ and $\vec{y}$ are two vectors with length n, $\rho(\vec{x}, \vec{y})$ is the Pearson's linear correlation which has the below formula (9):

$$\rho(\vec{x}, \vec{y}) = \frac{1}{n-1} \sum_{i=1}^{n} \left(\frac{x_i - \bar{x}}{s_x}\right)\left(\frac{y_i - \bar{y}}{s_y}\right) \tag{9}$$

wherein the sample standard deviation $s_x$ and $s_y$ have the below formula (10):

$$s_x = \sqrt{\frac{\sum_{i=1}^{n}(x_i - \bar{x})^2}{n-1}} \tag{10}$$

and wherein the sample mean $\vec{x}$ has the below formula (11):

$$\bar{x} = \frac{1}{n} \sum_{i=1}^{n} x_i \tag{11}$$

l) Pharmaceutical Composition or Drug

As used herein, the term "pharmaceutical composition" or "drug" as used interchangeably herein refers to any agent, whether a small molecule (e.g., a drug containing an active agent, typically a non-peptidic) or biologic (e.g., a peptide, protein or antibody based drug, including any with modifications, such as, but not limited to PEGylation) that can be used to treat a subject or patient suffering from at least one type of cancer.

m) Primer

The term "primer" refers to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an enzyme for nucleic acid polymerization (e.g., a DNA-dependent or RNA-dependent polymerase). The primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. Primers can have a length of about 15 to 50 nucleotides in length, preferably from about 20 to about 40 nucleotides in length. Primers contain also contain additional nucleotides. For example, primers used in SDA can include a restriction endonuclease recognition site 5' to the target binding sequence (See, U.S. Pat. Nos. 5,270,184 and 5,455,166), NASBA, and TMA primers can include an RNA polymerase promoter linked to the target binding sequence of the primer. Methods for linking such specialized sequences to a target binding sequence for use in a selected amplification reaction are well known to those skilled in the art. Additionally, in certain instances, a primer can be labeled with a detectable label.

The phrase "forward primer" refers to a primer that hybridizes (or anneals) with the target sequence (e.g., template strand). The phrase "reverse primer" refers to a primer that hybridizes (or anneals) to the complementary strand of the target sequence. The forward primer hybridizes with the target sequence 5' with respect to the reverse primer.

n) Probe

As used herein, the term "probe" refers to an oligonucleotide designed for use in connection with a CGH microarray, a SNPs microarray or any other microarrays known in the art that are capable of selectively hybridizing to at least a portion of a target sequence under appropriate conditions. In general, a probe sequence is identified as being either "complementary" (i.e., complementary to the coding or sense strand (+)), or "reverse complementary" (i.e., complementary to the antisense strand (−)). Probes can have a length of about 10-100 nucleotides, preferably about 15-75 nucleotides, most preferably from about 15-50 nucleotides.

o) Random Forests

The phrase "random forests" as used herein refers to a supervised learning algorithm described by Breiman in 2001 (See, Breiman, L., "Random Forests," *Machine Learning*, 45(1):5-32 (2001)) which uses a combination of tree predictors such that each tree depends on the values of a random vector sampled independently and with the same distribution for all trees in the forest.

Random Forests grow many classification trees. To classify a new object from an input vector, put the input vector down each of the trees in the forest. Each tree gives a classification, and it is said that the tree "votes" for that class. The forest chooses the classification having the most votes (over all the trees in the forest). Each tree is grown as follows:

1. If the number of cases in the training set is N, sample N cases at random—but with replacement, from the original data. This sample will be the training set for growing the tree.

2. If there are M input variables, a number m<<M is specified such that at each node, m variables are selected at random out of the M and the best splits on these m variables are used to split the node. The value of m is held constant during the forest growing.

3. Each tree is grown to the largest extent possible. There is no pruning.

The prediction error rate of random forest depends on two factors:

1. The correlation between any two trees in the forest. Increasing the correlation increases the forest error rate.

2. The strength of each individual tree in the forest. A tree with a low error rate is a strong classifier. Increasing the strength of the individual trees decreases the forest error rate.

B. Computational Algorithm and its Use in Genomic Classification of Tumors and Cancer Cell Lines As mentioned previously herein, the present invention relates to a method of classifying tumors and cell lines based on their genome-wide copy number (CN) patterns, assigning tumors and cancer cell lines to genomic subgroups based on their patterns of CN alterations and assembling panels of tumors and cancer cell lines to represent the genomic subgroups for a specific cancer type (See, FIG. 1). The above described methods employ a unique computational algorithm, which will be described in more detail herein.

Specifically, the present invention involves obtaining a plurality (m) of samples (where m is an integer from 1 to 5,000,000. For example, a plurality of samples can be two (2), five (5), ten (10), fifteen (15), twenty (20), twenty-five (25), fifty (50), one hundred (100), two hundred (200), five hundred (500) one thousand (1,000), ten thousand (10,000), fifty thousand (50,000), one hundred thousand samples (100,000), two hundred and fifty thousand samples (250,000), five hundred thousand (500,000), one million (1,000,000) samples, etc.) comprising tumor and cancer cell lines. After obtaining the tumor and cancer cell lines, the copy number and copy number alterations in the obtained selected tumor and cancer cell lines are detected using routine techniques known in the art. Tumors can be obtained from subjects suffering from one or more tumors or cancers (such as a subject suffering from human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adeno carcinomas, cystadeno carcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease). Such tumor cells can be obtained using routine techniques known in the art. For example, the tumors can be surgically dissected from a subject suffering or suspected of suffering from cancer and then immediately frozen, such as at −80° C.

Alternatively, samples of tumors and cancer cell lines can be obtained commercially or from public sources. Examples commercial or publically available sources that can be used to obtain or purchase such tumor or cancer cell lines include, but are not limited to, the American Type Culture Collection (ATCC), Manassus, Va.; Deutsche Sammlung von Mikroorganismen and Zellkulturen GmbH (DSMZ) Braunschweig, Germany; Cell Line Service (CLS), Germany; European Collection of Cell Cultures (ECACC), Salisbury, Great Britain.

Moreover, copy number and copy number alteration information for a variety of tumors and cancer cell lines can be obtained from a number of commercially or publically available sources, such as, but not limited to, on-line from the Gene Expression Omnibus (GEO), which is available from the National Center for Biotechnology Information (NCBI), on-line from the Broad Institute/Dana Farber Cancer Institute Melanoma Portal, on-line from the Dana Farber Cancer Institute web site, etc.

Examples of tumors and cancer cell lines that are available from commercially and publically available sources are shown below in Tables A-C. Specifically, Table A provides information on non-small cell lung cancer. Table B provides information on colorectal cancer. Table C provides information on melanoma.

TABLE A

| Cell Line | Source | ATCC catalog number | DSMZ catalog number | CLS catalog number | Reference to publication containing the data |
|---|---|---|---|---|---|
| CLS-54 | CLS | | | CLS-54 | |
| LX-289 | CLS | | | LX-289 | |
| SK-LU-1 | CLS | HTB-57 | | SK-LU-1 | |
| SK-MES-1 | CLS | HTB-58 | ACC 353 | SK-MES-1 | |
| H157 | Dana Farber Cancer Institute (DFCI) | | | | Zhao, X., et al., Cancer Res, 2005. 65(13): 5561-70 |
| H1819 | DFCI | CRL-5897 | | | Zhao, X., et al., Cancer Res, 2005. 65(13): 5561-70 |
| H2009 | DFCI | CRL-5911 | | | Zhao, X., et al., Cancer Res, 2005. 65(13): 5561-70 |
| H2882 | DFCI | | | | Zhao, X., et al., Cancer Res, 2005. 65(13): 5561-70 |
| H2887 | DFCI | | | | Zhao, X., et al., Cancer Res, 2005. 65(13): 5561-70 |
| HCC1171 | DFCI | | | | Zhao, X., et al., Cancer Res, 2005. 65(13): 5561-70 |
| HCC1359 | DFCI | | | | Zhao, X., et al., Cancer Res, 2005. 65(13): 5561-70 |
| HCC15 | DFCI | | | | Zhao, X., et al., Cancer Res, 2005. 65(13): 5561-70 |
| HCC193 | DFCI | | | | Zhao, X., et al., Cancer Res, 2005. 65(13): 5561-70 |
| HCC366 | DFCI | | | | Zhao, X., et al., Cancer Res, 2005. 65(13): 5561-70 |
| HCC461 | DFCI | | | | Zhao, X., et al., Cancer Res, 2005. 65(13): 5561-70 |
| HCC515 | DFCI | | | | Zhao, X., et al., Cancer Res, 2005. 65(13): 5561-70 |
| HCC78 | DFCI | | | | Zhao, X., et al., Cancer Res, 2005. 65(13): 5561-70 |
| HCC95 | DFCI | | | | Zhao, X., et al., Cancer Res, 2005. 65(13): 5561-70 |
| HOP-62 | DFCI | | | | Zhao, X., et al., Cancer Res, 2005. 65(13): 5561-70 |
| HOP-92 | DFCI | | | | Zhao, X., et al., Cancer Res, 2005. 65(13): 5561-70 |
| NCI-H266 | DFCI | | | | Zhao, X., et al., Cancer Res, 2005. 65(13): 5561-70 |
| NCI-H1437 | ATCC | CRL-5872 | | | |
| NCI-H1563 | ATCC | CRL-5875 | | | |
| NCI-H1568 | ATCC | CRL-5876 | | | |
| NCI-H1623 | ATCC | CRL-5881 | | | |
| NCI-H1651 | ATCC | CRL-5884 | | | |
| NCI-H1693 | ATCC | CRL-5887 | | | |
| NCI-H1734 | ATCC | CRL-5891 | | | |
| NCI-H1755 | ATCC | CRL-5892 | | | |
| NCI-H1793 | ATCC | CRL-5896 | | | |
| NCI-H1838 | ATCC | CRL-5899 | | | |
| NCI-H1944 | ATCC | CRL-5907 | | | |
| NCI-H1975 | ATCC | CRL-5908 | | | |
| NCI-H1993 | ATCC | CRL-5909 | | | |
| NCI-H2023 | ATCC | CRL-5912 | | | |
| NCI-H2073 | ATCC | CRL-5918 | | | |
| NCI-H2085 | ATCC | CRL-5921 | | | |
| NCI-H2087 | ATCC | CRL-5922 | | | |
| NCI-H2122 | ATCC | CRL-5985 | | | |
| NCI-H2126 | ATCC | CCL-256 | | | |
| NCI-H2228 | ATCC | CRL-5935 | | | |
| NCI-H2291 | ATCC | CRL-5939 | | | |
| NCI-H23 | ATCC | CRL-5800 | | | |
| NCI-H2342 | ATCC | CRL-5941 | | | |
| NCI-H2347 | ATCC | CRL-5942 | | | |
| NCI-H2405 | ATCC | CRL-5944 | | | |
| NCI-H522 | ATCC | CRL-5810 | | | |
| NCI-H647 | ATCC | CRL-5834 | | | |
| NCI-H838 | ATCC | CRL-5844 | | | |
| NCI-H920 | ATCC | CRL-5850 | | | |
| NCI-H969 | ATCC | CRL-5852 | | | |
| A549 | ATCC | CCL-185 | | | |
| Calu-3 | ATCC | HTB-55 | | | |
| HCC827 | ATCC | CRL-2868 | | | |
| Calu-6 | ATCC | HTB-56 | | | |
| H358 | ATCC | CRL-5807 | | | |
| H460 | ATCC | HTB-177 | | | |

TABLE B

| Cell Line | Source | ATCC catalog number | DSMZ catalog number | ECACC catalog number |
|---|---|---|---|---|
| DLD-1 | R4N2 | CCL-221 | ACC 278 | |
| HCT 116 | R4N2 | CCL-247 | | |
| HT-29 | R4N2 | HTB-38 | ACC 299 | |
| LoVo | R4N2 | CCL-229 | | |
| COLO 205 | R4N2 | CCL-222 | | |
| HCT-15 | R4N2 | CCL-225 | ACC 357 | |
| SW620 | R4N2 | CCL-227 | | |
| Caco-2 | ATCC | HTB-37 | | |
| COLO 320DM | ATCC | CCL-220 | | |
| HCT-8 | ATCC | (HRT-18) CCL-244 | | |
| LS 174T | ATCC | CL-188 | | |
| LS1034 | ATCC | CRL-2158 | | |
| LS411N | ATCC | CRL-2159 | | |
| LS513 | ATCC | CRL-2134 | | |
| NCI-H498 | ATCC | CCL-254 | | |
| NCI-H508 | ATCC | CCL-253 | | |
| NCI-H716 | ATCC | CCL-251 | | |
| NCI-H747 | ATCC | CCL-252 | | |
| SK-CO-1 | ATCC | HTB-39 | | |
| SW1116 | ATCC | CCL-233 | | |
| SW1417 | ATCC | CCL-238 | | |
| SW1463 | ATCC | CCL-234 | | |
| SW403 | ATCC | CCL-230 | | |
| SW837 | ATCC | CCL-235 | | |
| SW948 | ATCC | CCL-237 | | |
| CL-11 | DSMZ | | ACC 467 | |
| CL-14 | DSMZ | | ACC 504 | |
| CL-34 | DSMZ | | ACC 520 | |
| CL-40 | DSMZ | | ACC 535 | |
| COLO-206F | DSMZ | | ACC 21 | |
| COLO-678 | DSMZ | | ACC 194 | |
| SW-480 | DSMZ | | ACC 313 | |
| C170 | ECACC | | | 97071507 |
| LS 180 | ATCC | CL-187 | | |
| SW48 | ATCC | CCL-231 | | |

TABLE C

| Cell Line | Source | ATCC catalog number | DSMZ catalog number | Reference to publication containing the data |
|---|---|---|---|---|
| SKMEL19 | Broad Institute/Dana Farber Cancer Institute (Broad) | | | Lin, W. M., et al., Cancer Res, 2008. 68(3): 664-73 |
| SKMEL30 | Broad | | | Lin, W. M., et al., Cancer Res, 2008. 68(3): 664-73 |
| SKMEL63 | Broad | | | Lin, W. M., et al., Cancer Res, 2008. 68(3): 664-73 |
| SKMEL119 | Broad | | | Lin, W. M., et al., Cancer Res, 2008. 68(3): 664-73 |
| HS944 | Broad | CRL-7693 | | Lin, W. M., et al., Cancer Res, 2008. 68(3): 664-73 |
| WM1366 | Gene Expression Omnibus (GEO) | | | Greshock, J., et al., Cancer Res, 2007. 67(21): 10173-80. |
| WM88 | GEO | | | Greshock, J., et al., Cancer Res, 2007. 67(21): 10173-80. |
| WM3248 | GEO | | | Greshock, J., et al., Cancer Res, 2007. 67(21): 10173-80. |
| 1205Lu | GEO | CRL-2812 | | Greshock, J., et al., Cancer Res, 2007. 67(21): 10173-80. |
| WM35 | GEO | CRL-2807 | | Greshock, J., et al., Cancer Res, 2007. 67(21): 10173-80. |
| WM983 | GEO | | | Greshock, J., et al., Cancer Res, 2007. 67(21): 10173-80. |
| WM3211 | GEO | | | Greshock, J., et al., Cancer Res, 2007. 67(21): 10173-80. |
| M14 | GEO | | | Greshock, J., et al., Cancer Res, 2007. 67(21): 10173-80. |
| Malme-3M | GEO | HTB-64 | | Greshock, J., et al., Cancer Res, 2007. 67(21): 10173-80. |
| MeWo | GEO | HTB-65 | | Greshock, J., et al., Cancer Res, 2007. 67(21): 10173-80. |
| SKMEL2 | GEO | | | Greshock, J., et al., Cancer Res, 2007. 67(21): 10173-80. |
| SKMEL28 | GEO | | | Greshock, J., et al., Cancer Res, 2007. 67(21): 10173-80. |
| SKMEL5 | GEO | | | Greshock, J., et al., Cancer Res, 2007. 67(21): 10173-80. |
| UACC257 | GEO | | | Greshock, J., et al., Cancer Res, 2007. 67(21): 10173-80. |
| UACC62 | GEO | | | Greshock, J., et al., Cancer Res, 2007. 67(21): 10173-80. |
| WM122 | GEO | | | Greshock, J., et al., Cancer Res, 2007. 67(21): 10173-80. |
| WM13662 | GEO | | | Greshock, J., et al., Cancer Res, 2007. 67(21): 10173-80. |
| WM239A | GEO | | | Greshock, J., et al., Cancer Res, 2007. 67(21): 10173-80. |
| WM32112 | GEO | | | Greshock, J., et al., Cancer Res, 2007. 67(21): 10173-80. |
| WM32482 | GEO | | | Greshock, J., et al., Cancer Res, 2007. 67(21): 10173-80. |
| WM793B | GEO | CRL-2806 | | Greshock, J., et al., Cancer Res, 2007. 67(21): 10173-80. |
| WM882 | GEO | | | Greshock, J., et al., Cancer Res, 2007. 67(21): 10173-80. |
| WM983C | GEO | | | Greshock, J., et al., Cancer Res, 2007. 67(21): 10173-80. |
| 451Lu | GEO | CRL-2813 | | Greshock, J., et al., Cancer Res, 2007. 67(21): 10173-80. |
| 501MEL | GEO | | | Greshock, J., et al., Cancer Res, 2007. 67(21): 10173-80. |

Once the requisite tumors and cancer cell lines are obtained, genomic DNA is extracted from each of the tumors or cell lines using routine techniques known in the art, such as, phenol-chloroform extraction, salting out, digestion-free extraction or by the use of commercially available kits, such as the DNeasy or QIAamp kits available from (Qiagen, Valencia, Calif.). The genomic DNA obtained from each of the tumors or cell lines can then be modified or altered to facilitate the rest of the analysis. For example, primer or adapter sequences can be ligated to the genomic DNA using routine techniques known in the art. For example, the genomic DNA can first be digested with a restriction endonuclease (such as, for example HindIII, XbaI or combinations thereof) using routine techniques in the art (See, for example page 30 of the *GeneChip® Mapping* 100*K Assay Manual* 701684 Rev. 3, Affymetrix (2004)). Once digested, one or more primer or adapted sequences can be ligated to the digested genomic DNA. Preferably, the adapters used are those that recognize cohesive four base-pair overhangs. For example, a T4 DNA ligase can be used to ligate one or more adapters, such as Xba, Hind III, Nsp, Sty or any combinations thereof, to the digested genomic DNA. An example of a Xba adapter that can be used is a one having the sequence of: 5'TCTAGAGAT-CAGGCGTCTGTCGTGCTCATAA 3'(SEQ ID NO:2) which is commercially available from Affymetrix (See, page 128 of the *GeneChip® Mapping* 100*K Assay Manual* 701684 Rev. 3, Affymetrix (2004)). An example of a Hind III adapter that can be used is one having the sequence of 5' pACGTA-GATCAGGCGTCTGTCGTGCTCATAA3' (SEQ ID NO:3), which is commercial available from Affymetrix (See, page 129 of the *GeneChip® Mapping* 100*K Assay Manual* 701684 Rev. 3, Affymetrix (2004)). An example of a Nsp adapter that can be used is one having the sequences of: 5'ATTATGAG-CACGACAGACGCCTGATCTCATG 3' (SEQ ID NO:5) and 5' pAGATCAGGCGTCTGTCGTGCTCATAA 3' (SEQ ID NO:6), each of which are commercially available from Affymetrix (See, page 289 of the *GeneChip® Mapping* 500*K Assay Manual* PN 701930 Rev. 3, Affymetrix (2005-2006)). An example of a Sty adapter that can be used is one having the sequences of: 5' ATTATGAGCACGACAGACGCCT-GATCT 3' (SEQ ID NO: 7) and 5' pCWWGAGATCAG-GCGTCTGTCGTGCTCATAA 3' (SEQ ID NO:8), each of which are commercially available from Affymetrix (See, page 292 of the *GeneChip® Mapping* 500*K Assay Manual* PN 701930 Rev. 3, Affymetrix (2005-2006)). Techniques for using a T4 DNA ligase to ligate a Xba and a Hind III adapter to genomic DNA are described, for example, on page 33 of the *GeneChip® Mapping* 100*K Assay Manual* 701684 Rev. 3, Affymetrix (2004). Techniques for using a T4 DNA ligase to ligate a Nsp and a Sty adapter to genomic DNA are described, for example, on page 253 of the *GeneChip® Mapping* 500*K Assay Manual* PN 701930 Rev. 3, Affymetrix (2005-2006)).

The DNA is then amplified using routine nucleic acid amplification methods that employs certain amplification conditions and amplification reagents. As used in this paragraph in connection with DNA amplification, the term "amplification conditions" refers to conditions that promote annealing and/or extension of primer sequences. Such conditions are well-known in the art and depend on the amplification method selected. For example, PCR amplification conditions generally comprise thermal cycling, e.g., cycling of the reaction mixture between two or more temperatures. In isothermal amplification reactions, amplification occurs without thermal cycling although an initial temperature increase may be required to initiate the reaction. Amplification conditions encompass all reaction conditions including, but not limited to, temperature and temperature cycling, buffer, salt, ionic strength, pH, and the like. As also used in this paragraph in connection with DNA amplification, the phrase "amplification reagents" refers to reagents used in nucleic acid amplification reactions. The types of amplification reagents will vary depending upon the type of nucleic acid amplification method selected. The selection of amplification reagents for use in a nucleic acid amplification method are well known to those skilled in the art. Examples of amplification reagents known in the art, include, but are not limited to, buffers, reagents, enzymes having reverse transcriptase and/or polymerase activity or exonuclease activity; enzyme cofactors such as magnesium or manganese; salts; and deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). Nucleic acid amplification methods include, but are not limited to, the Polymerase Chain Reaction (PCR). PCR is described in a number of references, such as, but not limited to, "*PCR Protocols: A Guide to Methods and Applications*", M. A. Innis (Ed.), Academic Press: New York (1990); "*PCR Strategies*", M. A. Innis (Ed.), Academic Press: New York (1995); "*Polymerase chain reaction: basic principles and automation in PCR. A Practical Approach*", McPherson et al. (Eds.), IRL Press: Oxford (1991); Saiki et al., *Nature*, 324:163 (1986); and U.S. Pat. Nos. 4,683,195, 4,683,202 and 4,889,818, each of which is incorporated herein by reference in its entirety. Variations of PCR including, TaqMan®-based assays (See, Holland et al., *Proc. Natl. Acad. Sci. USA,* 88: 7276-7280 (1991)), and reverse transcriptase polymerase chain reaction (or RT-PCR, described in, for example, U.S. Pat. Nos. 5,322,770 and 5,310,652, each of which is incorporated by reference) are also included.

Generally, in PCR, a single primer or pair of primers is added to a DNA obtained from the tumors or cancer cell lines described above in excess to hybridize to the complementary strands of the target nucleic acid. If the genomic DNA obtained from the tumors or cancer cell lines is digested and ligated to primer or adapter sequences, then it is preferred that one of the primers used in the amplification method recognize the adapter sequences. It is also preferred that the primer(s) used in the amplification method, such as that described in the above paragraph, amplify fragments in the 250 to 2000 base pair size range. Examples of a primer that can be used in the present invention is PCR Primer 001 which has the sequence 5'ATTATGAGCACGACAGACGCCTGATCT 3' (SEQ ID NO:1 and PCR Primer 002 which has the sequence 5'ATTAT-GAGCACGACAGACGCCTGATCT 3' (SEQ ID NO: 4) which are each commercially available from Affymetrix (See, page 128 of the *GeneChip® Mapping* 100*K Assay Manual* 701684 Rev. 3, Affymetrix (2004) (PCR Primer 001) and page 289 of the *GeneChip® Mapping* 500*K Assay Manual* PN 701930 Rev. 3, Affymetrix (2005-2006) (PCR Primer 002). The primer(s) are each extended by a DNA polymerase using the target sequence as a template. The extension products become targets themselves after dissociation (denaturation) from the original target strand. New primer(s) are then hybridized and extended by the polymerase, and the cycle is repeated to exponentially increase the number of copies of amplified DNA. Examples of DNA polymerases capable of producing primer extension products in PCR reactions include, but are not limited to, *E. coli* DNA polymerase I, Klenow fragment of DNA polymerase I, T4 DNA polymerase, thermostable DNA polymerases isolated from *Thermus aquaticus* (Taq), available from a variety of sources (e.g., Perkin Elmer, Waltham, Mass.), *Thermus thermophilus* (USB Corporation, Cleveland, Ohio), *Bacillus stereothermophilus*

(Bio-Rad Laboratories, Hercules, Calif.), AmpliTaq Gold® Enzyme (Applied Biosystems, Foster City, Calif.), recombinant *Thermus thermophilus* (rTth) DNA polymerase (Applied Biosystems, Foster City, Calif.) or *Thermococcus litoralis* ("Vent" polymerase, New England Biolabs, Ipswich, Mass.). RNA target sequences may be amplified by reverse transcribing (RT) the mRNA into cDNA, and then performing PCR, as described above. Alternatively, a single enzyme may be used for both steps as described in U.S. Pat. No. 5,322,770, which is herein incorporated by reference.

Upon completion of the amplification, the resulting amplified DNA can be purified, using routine techniques in the art (such as, for example, by using a Qiagen MinElute 96 UF PCR Purification system which is available from Qiagen, Valencia, Calif., a protocol for which is described on page 42 of the *GeneChip® Mapping* 100*K Assay Manual* 701684 Rev. 3, Affymetrix (2004) or a Clontech Clean-Up Plate, a protocol for which is described on page 74 of the *GeneChip® Mapping* 500*K Assay Manual* PN 701930 Rev. 3, Affymetrix (2005-2006)). After purification, the amplified DNA is then fragmented using routine techniques known in the art, such as by sonication or by using an enzyme, such as DNase I. After fragmentation, the DNA is labeled with a detectable label. Methods for labeling DNA and fragments of DNA are well-known to those skilled in the art. Reviews of labeling protocols and label detection techniques can be found, for example in, L. J. Kricka, *Ann. Clin. Biochem.*, 39:114-129 (2002); van Gijlswijk et al., *Expert Rev. Mol. Diagn.*, 1:81-91 (2001); and Joos et al., *J. Biotechnol.*, 35:135-153 (1994). Standard nucleic acid labeling methods include: incorporation of radioactive agents, direct attachments of fluorescent dyes (See, Smith et al., *Nucl. Acids Res.*, 13:2399-2412 (1985)) or of enzymes (See, Connoly et al., *Nucl. Acids. Res.*, 13:4485-4502 (1985)); chemical modifications of nucleic acid molecules making them detectable immunochemically or by other affinity reactions (See, Broker et al., *Nucl. Acids Res.*, 5:363-384 (1978); Bayer et al., *Methods of Biochem. Analysis*, 26:1-45 (1980); Langer et al., *Proc. Natl. Acad. Sci. USA*, 78:6633-6637 (1981)); Richardson et al., *Nucl. Acids Res.*, 11:6167-6184 (1983); Brigati et al., *Virol.*, 126:32-50 (1983); Tchen et al., *Proc. Natl. Acad. Sci. USA*, 81:3466-3470 (1984); Landegent et al., *Exp. Cell Res.*, 15:61-72 (1984); and A. H. Hopman et al., *Exp. Cell Res.*, 169:357-368 (1987)); and enzyme-mediated labeling methods, such as random priming, nick translation, PCR and tailing with terminal transferase (For a review on enzymatic labeling, see, for example, Temsamani et al., *Mol. Biotechnol.*, 5:223-232 (1996)).

Any of a wide variety of detectable labels can be used. Suitable detectable labels include, but are not limited to, various ligands, radionuclides (e.g., $^{32}P$, $^{35}S$, $^{3}H$, $^{14}C$, $^{125}I$, $^{131}I$, and the like); fluorescent dyes; chemiluminescent agents (e.g., acridinium esters, stabilized dioxetanes, and the like); spectrally resolvable inorganic fluorescent semiconductor nanocrystals (e.g., quantum dots), metal nanoparticles (e.g., gold, silver, copper and platinum) or nanoclusters; enzymes (e.g., horseradish peroxidase, beta-galactosidase, luciferase, alkaline phosphatase); colorimetric labels (e.g., dyes, colloidal gold, and the like); magnetic labels (e.g., Dynabeads™); and biotin, dioxigenin or other haptens and proteins.

Once the amplified, fragmented DNA is labeled with a detectable label, it is hybridized to a microarray using routine techniques known in the art. The microarray can contain oligonucleotides, genes or genomic clones that can be used in Comparative Genomic Hybridization (CGH) to look for genomic gains and losses or for a change in the number of copies of a particular gene involved in a disease state. Alternatively, the microarray can contain oligonucleotides, genes or genomic clones that contain mutations or polymorphisms, such as single nucleotide polymorphisms (SNPs). Microarrays can be made using routine techniques known in the art. Alternatively, commercially available microarrays can be used. Examples of microarrays that can be used are the Affymetrix GeneChip® Mapping 100K Set SNP Array (See Matsuzaki, H., et al., "Genotyping over 100,000 SNPs on a pair of oligonucleotide arrays," *Nat Methods.* 1:109-11 (2004)); the Affymetrix GeneChip® Mapping 250K Assay Kits (such as the GeneChip® Human Mapping 250K Nsp Array or the GeneChip® Human Mapping 250K Sty Array) or the Affymetrix GeneChip® Mapping 500K Array Set, each of which is commercially available from Affymetrix, Inc., Santa Clara, Calif.), the Agilent Human Genome aCGH Microarray 44B (available from Agilent Technologies, Inc., Santa Clara, Calif.), Illumina microarrays (Illumina, Inc., San Diego, Calif.), Nimblegen aCGH microarrays (Nimblegen, Inc., Madison, Wis.), etc.

After hybridization, the microarray is washed using routine techniques known in the art. After washing, the microarray placed into a reader or scanner for analysis. Examples of a reader or scanner that can be used are the GeneChip® Scanner 3000 G7 (available from Affymetrix, Inc., Santa Clara, Calif.), the Agilent DNA Microarray Scanner (available from Agilent Technologies, Inc., Santa Clara, Calif.), GenePix 4000B (available from Molecular Devices, Sunnyvale, Calif.), etc. Signals gathered from the probes contained in the microarray can be analyzed using commercially available software, such as those provided by Affymetrix or Agilent Technologies. For example, if the GeneChip® Scanner 3000 G7 from Affymetrix is used, the Affymetrix GeneChip® Operating Software can be used. The Affymetrix GeneChip® Operating Software collects and extracts the raw or feature data (signals) from the Affymetrix GeneChip® Scanners, which detect the signals from all the probes. The raw or feature data can be stored electronically in one of any suitable file formats, such as, but not limited to, as a CEL file (The format of the CEL file is an ASCII text file similar to the Windows INI format), as a CHP file, as a CNT file, as a metaprobe set file or even as a plain text file.

The data collected and extracted from the microarray is processed to provide a data set comprising the copy number alteration (e.g., a gain or a loss in copy number) information from at least one locus from each chromosome from each tumor and cancer cell line sample. This copy number alteration information is used to define regions (or patterns) of copy number alterations on a genome-wide scale for each of these samples. Such processing can be done using algorithms known in the art, such as, but not limited to, Binary Circular segmentation (See, Olshen, A. B., et al., "Circular binary segmentation for the analysis of array-based DNA copy number data.", *Biostatistics* 5(4):557-72 (2004)), Gain and Loss Analysis of DNA (GLAD) (See, Hupe, P., et al., "Analysis of array CGH data: from signal ratio to gain and loss of DNA regions.", *Bioinformatics*, 20(18):3413-22 (2004)), Hidden Markov Model-based approaches (See, Fridlyand, J., et al., "Hidden Markov models approach to the analysis of array CGH data." *Journal of Multivariate Analysis*, 90(1):132-153 (2004); Zhao, X., et al., "An integrated view of copy number and allelic alterations in the cancer genome using single nucleotide polymorphism arrays." *Cancer Res*, 64(9):3060-71 (2004)), or clustering-based methods (See, Wang, P., et al., "A method for calling gains and losses in array CGH data.", *Biostatistics*, 6(1): 45-58 (2005)), etc. Alternatively, commercially available software can be used, such as, but are not limited to, the Partek® Genomic Suite™ software, such as version 6.08.0103 (available from Partek®, St. Louis, Mo.), GenePattern (available on-line; See, Reich M, Liefeld T, Gould J, Lerner J, Tamayo P, Mesirov J P (2006), "GenePattern 2.0", *Nature Genetics*, 38:5, 500-501 (2006)), and dChip (which is available on-line; See, Cheng Li et al., "Model-based analysis of oligonucleotide arrays: model validation, design issues and standard error application," *Genome Biology* 2(8): research0032.1-0032.11 (2001); Cheng Li et al., "Model-based analysis of oligonucleotide arrays: Expression index computation and outlier detection," *Proc. Natl. Acad. Sci. Vol.* 98, 31-36 (2001)).

For example, if the Partek® Genomic Suite™ software, such as version 6.08.0103 is used, CEL files for tumor and cancer cell line samples containing the signals from all the probes in the microarray detected by the scanners can be loaded into the software. The copy numbers are calculated by comparing the signal intensities for the tumor or cancer cell line samples determined from the microarray to those in a reference or control after correction to a preset baseline (the number used to establish the preset baseline is not critical and is an integer (n), where n is 1 to 100. For example, the preset baseline can be 2). The reference or control used can be a set of normal tissue samples or paired normal tissues from the same patients as the tumor samples measured by the same microarray platform. The reference or control is an integer (n) of from about 1 to 1000 samples. For example, the reference or control can comprise at least 5 samples, at least 10 samples, at least 15 samples, at least 20 samples, at least 25 samples, at least 30 samples, at least 35 samples, at least 40 samples, at least 45 samples, at least 50 samples, at least 75 samples, at least 100 samples, at least 150 samples, at least 200 samples, etc.

The resulting copy number data is then segmented and copy number alteration regions are detected in each sample. The segmentation and detection of copy number alteration regions can be obtained using certain control parameters. For example, the following control parameters can be used: (i) that a copy number region must contain at least 100 probes, (ii) that the p-value comparing the mean copy number of the copy number region versus the adjacent copy number regions must be less than 0.00001, and (iii) that the signal/noise ratio of the transition must be greater than 0.1. The copy number alteration regions can be detected when the mean copy numbers in these regions is statistically less than about 1.65 (for a deletion) (such as less than 1.65, less than 1.60, less than 1.55, less than 1.50, less than 1.45, less than 1.40, less than 1.35, less than 1.30, less than 1.25, etc.) or greater than about 2.65 (for a gain) (such as greater than 2.65, greater than 2.70, greater than 2.75, greater than 2.80, greater than 2.85, greater than 2.90, greater then 3.0, greater than 3.05, etc.) with P values below 0.01.

Because tumor samples can contain a significant percentage (the phrase "significant percentage meaning, greater than 30%, greater than 40%, greater than 50%, greater than 60%, greater than 70%, greater than 80% or greater than 90%) of normal (e.g., non-cancerous) cells which can dilute the signal of a copy number alteration, the data set is reviewed to identify and eliminate any copy number alteration information obtained from samples contaminated by significant percentage of normal cells. A machine learning algorithm can be used to identify and capture the difference between the copy number patterns of tumor and cancer cell line samples and those of normal samples. Such an algorithm can be used to identify and eliminate tumor samples contaminated by normal cells from further analysis. Thus, the machine learning algorithm serves as a data quality control for the data set and is referred to herein as a "data quality control algorithm".

The data quality control algorithm involves selecting a subset of samples with the highest number of copy number alteration regions from the tumor and cancer cell line samples as previously described herein (hereinafter the "first sample set"). A normal set of samples is also selected (hereinafter "the second sample set"). These first and second sample sets are used as a training set to develop a machine learning algorithm to classify samples as either being "normal" or "tumor" samples by tuning the parameters of the algorithm to best represent the difference between first and second sample set. The trained classifier is applied to the remaining tumor or cancer cell line samples to assign a probability score for containing normal cell contamination to each sample. This probability score represents the probability of each sample being contaminated by normal cells. Samples having a contamination probability over fifty percent (50%) are excluded or eliminated from the data set and hence from the subsequent clustering analysis. Examples of machine learning algorithms that can be used include Random Forests, Support Vector Machine (SVM) (See, Vapnik, V., *The nature of statistical learning theory*. Springer-Verlag, New York (1995)), Recursive-SVM (See, Zhang, X., et al., "Recursive SVM feature selection and sample classification for mass-spectrometry and microarray data," *BMC Bioinformatics*, 7:197 (Apr. 10, 2006)), Least-Angle Regression (LARS) (Efron, B., et al., "Least angle regression," *Annals of Statistics*, 32:407-451 (2004)), etc.

Because copy number data obtained from microarrays tends to be highly dense and noisy, the copy number data can be smoothed to decrease the noise level and reduce the dimensionality (also referred to as "dimension reduction") and the complexity of the dataset. Smoothing of the data set can be done by first detecting significantly gained or deleted copy number regions in each sample using routine techniques known in the art. Once such regions are identified, adjacent regions can be merged if they have similar copy number changes and if the distances between these regions are less than 500 kilobases. The entire genome can then be segmented using the union of break points from all samples in the data and the copy number of each segment can be calculated by averaging the copy number of SNPs probes within each segment (See, Carrasco, et al., "High-resolution genomic profiles define distinct clinico-pathogenetic subgroups of multiple myeloma patients," *Cancer cell*, 9:313-325 (2006)). As a result of this data smoothing, better resolution of the copy number gains and deletions from each of the samples in the data set can be obtained.

After data smoothing and dimension reduction, the data set is subjected to an unsupervised clustering method to obtain an overview of the relative similarity between each of the tumor and cancer cell line samples and to obtain an estimate (eg., a rough estimate) of the number of subgroups (which is also referred to herein as r subgroups) that exist in the data thus far and that are to eventually be clustered. After data smoothing and dimension reduction, unsupervised clustering methods using the Personal linear dissimilarity algorithm are applied to the smoothed tumor and cell line copy number data which is referred to as the "Data Set" (V). The clustering patterns can be plotted and visually inspected to derive a range of possible numbers of subgroups, r, in the Data Set (the range of possible numbers of subgroups in the Data Set will be an integer (n) from 1 to 100). Examples of unsupervised clustering methods that can be used include, but are not limited to, hierarchical clustering, Principal Components Analysis (PCA) (See, Pearson, K., "On Lines and Planes of Closest Fit to Systems of Points in Space," *Philosophical Magazine*. 2:559-572 (1901)) or Multidimensional Scaling (MDS) (See, Borg, I., and P. Groenen, *Modern Multidimensional Scaling: theory and applications.* Springer, N.Y. (2005)). The numbers of subgroups (which are each referred to as "r value", where each r value is an integer from 1 to 100) are then used as input in the clustering analysis using genomic non-negative matrix factorization ("gNMF").

In previous applications of gNMF to cluster CGH data (See, Maher, E. A., et al., "Marked genomic differences characterize primary and secondary glioblastoma subtypes and identify two distinct molecular and clinical secondary glioblastoma entities," *Cancer Res.,* 66:11502-13 (2006); Carrasco, D. R., et al., "High-resolution genomic profiles define distinct clinico-pathogenetic subgroups of multiple myeloma patients," *Cancer Cell,* 9:313-25 (2006)), the algorithm was stopped when the subgroup assignments of tumor or cancer cell line samples did not change after a pre-defined number of steps (e.g., 100). Based on tests with simulated data as well as actual CGH data, it is believed that this criterion stops (e.g. terminates) the gNMF algorithm too early. Therefore, the gNMF algorithm can be modified so that after a selected number of steps (where the selected number of steps is not critical and is an integer (n) from 1 to 1000, such as, for example, 5 steps, 10 steps, 25 steps, 50 steps, 100 steps, 200 steps, etc.) of multiplicative updating, the divergence of the algorithm from the Data Set is calculated using the below formula (1):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (1)$$

wherein the $V_{ij}$ is the $i^{th}$ row and $j^{th}$ column of the Data Set, $(WH)_{ij}$ is the $i^{th}$ row and $j^{th}$ column of matrix (W*H), i runs from 1 to n and n is the number of segments in the smoothed Data Set V, and j runs from 1 to m and m is the number of samples in the Data Set.

Using the above formula, the iterative algorithm stops (also referred to herein as the "stop criterion") if the divergence calculated above does not decrease by more than about 0.001% when compared to the divergence calculated for the previous or prior selected number of steps (for example, 100) of multiplicative updating for the algorithm. This modification to the gNMF algorithm has been found to significantly improve the accuracy of the clustering.

Because gNMF is a stochastic procedure, the algorithm can generate different outcomes when started from different initial values. To further improve the performance of the clustering algorithm, a new multiple initiation strategy was developed. For each Data Set, the strategy involves using the above described stop criterion and randomly starting or repeating the gNMF algorithm for a select number of runs (the select number of runs that the algorithm can be randomly started or repeated is an integer (n) from 1 to 1000, such as for example, 1, 5, 10, 15, 20, 25, 30, 35, 40, 45, 50, 55, 60, 65, 70, 75, 80, 85, 90, 95, 100, 125, 150, 175, 200, 225, 250, 275, 300, 350, etc). Once the algorithm has completed its randomly selected number of runs, the Pearson correlation coefficient matrix of H for the each of these run is calculated using the below formula (2):

$$C_{i,j} = \rho(H_{\cdot,i}, H_{\cdot,j}) = \frac{\frac{1}{r-1}\sum_{k}(H_{k,i} - \overline{H_{\cdot,j}})(H_{k,j} - \overline{H_{\cdot,j}})}{s_{H_{\cdot,i}}s_{H_{\cdot,j}}} \quad (2)$$

wherein C is the correlation matrix, is the $i^{th}$ row and $j^{th}$ column in the matrix C, $H_{\cdot,i}$ and $H_{\cdot,j}$ are the $i^{th}$ and $j^{th}$ column vector in matrix H, $\rho(H_{\cdot,i}, H_{\cdot,j})$ is the Pearson correlation coefficient between $H_{\cdot,i}$ and $H_{\cdot,j}$, i and j run from 1 to m and m is the number of samples in the data set, k runs from 1 to r and r is the number of subgroups (determined previously herein). Once the Pearson correlation coefficient matrix of H for each run is determined, the correlation matrices are averaged. The final clustering result can be derived by running an unsupervised clustering method (e.g., such as a hierarchical clustering algorithm) using 1 minus the average correlation matrix as the distance matrix and cutting the dendrogram into r subgroups.

For example, if the gNMF algorithm is randomly run 200 times, after the 200 runs, the Pearson correlation coefficient matrix of H from the output of each of the 200 random gNMF runs is calculated using the above described formula. Then the correlation matrices over the 200 runs are then averaged. The final clustering result can be derived by running a hierarchical clustering algorithm using 1 minus the average correlation matrix as the distance matrix and cutting the dendrogram into r subgroups.

Once the final clustering result is obtained, Cophenetic correlation coefficient, Bayesian Information Criterion (BIC) or a combination of the Cophenetic correlation and BIC is then used to select the best model (namely, the best number of clusters and the best assignment of each sample into one of the clusters) most reflective of the distribution of the genetic patterns of these tumor and cell line samples. Lognormal distribution can be used in this analysis as it is widely used to fit DNA copy numbers (See, Hodgson et al, *Nature,* 29:459 (2001)). To calculate the likelihood, it can be assumed that samples in each cluster came from the same multi-lognormal distribution where the mean copy number of each segment followed a lognormal distribution. If the correlation between segments is weak, independence can be assumed between segments in the calculation. In this instance, the resulting log-likelihood formula is shown below in formula (12):

$$\ln L = \frac{1}{2}\ln(2\pi)\sum_{i=1}^{r}\sum_{j=1}^{n_i}\sum_{t=1}^{m}\frac{(y_{ijt} - \mu_{it})^2}{2\sigma_{it}^2}\ln(\sigma_{ij}) \quad (12)$$

wherein r is the number of clusters, $n_i$ is the number of samples in cluster i, m is the number of segments, $y_{ijt}$ is the log transformed copy number of the $t^{th}$ segment of the $j^{th}$ sample in the $i^{th}$ cluster, $\mu_{it}$ is the average of log transformed copy numbers of the $t^{th}$ segment in the $i^{th}$ cluster, and $\sigma_{it}$ is the standard deviation of log transformed copy numbers of the $t^{th}$ segment in the $i^{th}$ cluster. Then the number of parameters, k, in the specified model would be 2×r×m.

Many times, when using both Cophenetic correlation coefficient and BIC as a criterion to select the best model in unsupervised clustering, these two algorithms will often select the same model.

A 10-fold stability test procedure can be used to assess the stability of the clustering results. The 10-fold stability test can be performed as follows. After running gNMF on the data set and assigning the samples to clusters, at least about 10% of the tumor and cancer cell line samples are left out and the modified gNMF algorithm described above is run a second time on the remaining 90% of the tumor and cancer cell line samples (if at least about 15% of the tumor and cancer cell line samples are left out then the gNMF algorithm described above would be run a second time on the remaining 85% of the tumor and cancer cell line samples, etc.). The number of samples assigned to a different cluster as a result of this permutation is then calculated. The test is repeated a selected number of times (the test can be repeated from 1 to 1000 times. For example, the test can be repeated, 1 time, 20 times, 25 times, 50 times, 100 times, 200 times, 500 times, 750 times, 1000 times, etc.) to derive an error rate using routine techniques known in the art. This error rate represents the stability of the clustering result with respect to the permutation of the tumor and cancer cell line samples. This 10-fold stability test can be used on unsupervised clustering methods (e.g., hierarchical clustering) using the same data sets (the tumor and cancer cell line samples).

C. Assembly of Panels of Tumors and Cell Lines Based on the Genomic Classification of Tumors and Cancer Cell Lines Using the methods described above in Section B, tumor and cancer cell lines of the same tumor type can be classified into genomic subgroups. First, a plurality (m) of tumors of the cancer types of interest and cancer cell lines are clustered into distinct subgroups using the methodology described above in Section B. From each of these subgroups, at least one cell line is selected and added to the panel. The resulting panel will thus represent all genomic subtypes of the cancer type of interest. These panels of tumor and cancer cell lines can be used as preclinical models for pharmaceutical composition or drug testing for each specific subcategory of cancer, thus providing comprehensive coverage of the genomic diversity of the tumor type under consideration. Because of the commonly observed correlation between the genomic composition of a tumor and its phenotype (including drug response), it is expected that the pattern of copy number alterations will correlate with drug sensitivity in cell lines and will determine drug response in patients.

By way of example and not of limitation, examples of the present invention shall now be given.

EXAMPLE 1

A General Methodology and Algorithm for Assembling Panels of Cell Lines and/or Xenografts 1. DNA Extraction and Hybridization to SNPs Arrays.

The Affymetrix GeneChip® Mapping 100K Set SNP array (See, Matsuzaki, H., et al., "Genotyping over 100,000 SNPs on a pair of oligonucleotide arrays," *Nat Methods,* 1:109-11 (2004); commercially available from Affymetrix, Inc., Santa Clara, Calif.) covers 116,204 single-nucleotide polymorphism (SNP) loci in the human genome with a mean inter-marker distance of 23.6 kb. The array set includes two chips, Xba240 and Hind240. The chips and reagents were obtained from Affymetrix and the assays were carried out according to the manufacturer's instructions. Briefly, 30 mg tissue from each tumor or 5 million cells from each cell line were used to extract high molecular weight, genomic DNA using the DNAeasy kit (Qiagen, Valencia, Calif.). 250 ng of genomic DNA were digested with either HindIII or XbaI and then ligated to Adaptor Xba (5' TCTAGAGATCAGGCGTCT-GTCGTGCTCATAA 3'(SEQ ID NO:2)) and Adaptor Hind III (5' pACGTAGATCAGGCGTCTGTCGTGCTCATAA 3' (SEQ ID NO:3)) each of which recognize the cohesive four base-pair (bp) overhangs using a T4 DNA ligase as described on page 33 of the *GeneChip® Mapping 100K Assay Manual* 701684 Rev. 3, Affymetrix (2004)). The generic primer, PCR Primer, 001, having the sequence of 5'ATTATGAGCACGA-CAGACGCCTGATCT 3' (SEQ ID NO:1), which is commercially available from Affymetrix (See, *GeneChip® Mapping 100K Assay Manual* 701684 Rev. 3, Affymetrix (2004)) that recognizes the adapter sequence was used to amplify adapter-ligated DNA fragments with PCR conditions optimized to preferentially amplify fragments in the 250-2,000 bp size range in a GeneAmp PCR System 9700 (Applied Biosystems, Foster City, Calif.) (See, page 36 of the *GeneChip® Mapping 100K Assay Manual* 701684 Rev. 3, Affymetrix (2004)). After purification with a Qiagen MinElute 96 UF PCR purification system (See page 42 of the *GeneChip® Mapping 100K Assay Manual* 701684 Rev. 3, Affymetrix (2004)), the PCR product was fragmented (See, page 45 of the *GeneChip® Mapping 100K Assay Manual* 701684 Rev. 3, Affymetrix (2004)), labeled with biotin (See page 49 of the *GeneChip® Mapping 100K Assay Manual* 701684 Rev. 3, Affymetrix (2004)) and hybridized to the GeneChip® Mapping 100K Set for 16 hours (See, page 51 of the *GeneChip® Mapping 100K Assay Manual* 701684 Rev. 3, Affymetrix (2004)). The arrays were washed using the Affymetrix Fluidics Station 450 and scanned using a GeneChip® Scanner 3000 7G (Affymetrix, Santa Clara, Calif.) (See, page 57 of the *GeneChip® Mapping 100K Assay Manual* 701684 Rev. 3, Affymetrix (2004)). The Affymetrix GeneChip® Operating Software (GCOS) collected and extracted feature data from Affymetrix GeneChip® Scanners (See, page 93 of the *GeneChip® Mapping 100K Assay Manual* 701684 Rev. 3, Affymetrix (2004)).

2. Copy Number Determination and Detection of Copy Number Alterations.

Partek® Genomic Suite™ software (version 6.08.0103) was used for low-level processing of the data to determine the copy numbers of each locus and define regions of copy number alteration. CEL files containing signals for all SNPs probes were loaded into the software, and copy numbers were calculated by comparing the signal intensities for tumor or cell line samples to those for a reference set of 48 normal female tissue samples, corrected to a baseline of 2. The reference set can also consist of other sets of normal samples, or paired normal tissues from the same patients of the tumor samples, measured by the same microarray platform.

The resulting probe-level copy number data were segmented and the copy number alteration regions were detected in each sample. Specifically, probe-level copy numbers were segmented into regions using the following control parameters: (i) a region must contain at least 100 probes, (ii) the p-value comparing the mean copy number of the region versus the adjacent regions must be less than 0.00001, and (iii) the signal/noise ratio of the transition must be greater than 0.1. Then the copy number alteration regions were detected when the mean copy numbers in these regions were statistically less than 1.65 (deletion) or greater than 2.65 (gain) with P values below 0.01.

3. Data Quality Control.

Tumor samples may contain a significant percentage of normal cells, which will dilute the signal of copy number alteration. A machine learning algorithm was developed to capture the difference between copy number patterns of tumor and normal samples and used to identify and eliminate normal contaminated samples from further analyses. First, a subset of samples with the highest number of copy number alteration regions and a set of normal samples were selected. These two groups of samples were used as a training set to train a machine learning algorithm [Random Forests (See, Breiman, L., "Random Forests," *Machine Learning,* 45(1):5-32 (2000))] to classify normal and tumor samples by tuning the parameters to best represent the difference between tumor and normal samples. The trained classifier was applied to the rest of samples to assign a score to each sample that represented the probability of it being contaminated by normal cells. Samples with normal contamination probability over 50% were excluded from clustering analysis.

4. Data Smoothing and Dimension Reduction.

Because of the high density of copy number data obtained by SNPs microarrays and the significant amount of noise, the copy number data need to be smoothed to decrease the noise level and reduce the dimensionality and complexity of the clustering analysis. After detecting significantly gained or deleted regions in each sample, the adjacent regions were merged if they had similar copy number changes and the distance between them was less than 500 kb. The DNA segments were formed by using the union of break points from all samples in a data set. The average copy number of probes within each segment was used for further analysis. This step allowed for a clearer resolution of DNA gains and deletions in a high-throughput analysis.

5. Pilot Clustering Analysis Using Hierarchical Clustering to Determine the Possible Number of Subgroups.

Although widely used in many applications, hierarchical clustering has a number of drawbacks for genomic studies. First, it cannot consistently and objectively estimate the number of subgroups in a dataset. Second, hierarchical clustering patterns can be unstable. Specifically, a clustering pattern could change dramatically when a small number of samples is added to or deleted from a dataset. Additionally, in this analysis, a much higher error rate was observed when the 10-fold stability test result of hierarchical clustering was compared with that for genomic Non-negative Matrix Factorization (gNMF; See, Section 8 below).

Nevertheless, hierarchical clustering can serve as a useful tool to quickly derive an overview of the relative similarity between samples and provide a rough estimate of the possible number of subgroups that exist in the data. For each data set, the tumor and cell line CGH data was hierarchically clustered using Pearson linear dissimilarity. The hierarchical clustering patterns were plotted and visually inspected to derive a range of possible numbers of subgroups in the dataset. These numbers were then used as input in the clustering analysis using gNMF (See Section 6 below).

6. gNMF Clustering of the Tumor and Cell Line CGH Data.

NMF was first adopted in genomics for analysis of gene expression data (See, Brunet, J. P., et al., Metagenes and molecular pattern discovery using matrix factorization. *Proc Natl Acad Sci USA*. 101:4164-9 (2004)). The methodology was then adapted for use in the analysis of gene copy number data (See, Maher, E. A., et al., "Marked genomic differences characterize primary and secondary glioblastoma subtypes and identify two distinct molecular and clinical secondary glioblastoma entities," *Cancer Res*. 66:11502-13 (2006); Carrasco, D. R., et al., "High-resolution genomic profiles define distinct clinico-pathogenetic subgroups of multiple myeloma patients," *Cancer Cell*. 9:313-25 (2006)). Given a n×m matrix V of smoothed copy number data for a set of samples (namely, in the data set), where n is the number of segments and m is the number of samples, the gNMF algorithm factorizes the matrix V into an n×r matrix W and a r×m matrix H as shown in the below formula (5):

$$V = W*H + e \quad (5)$$

In the above formula (5), W can be viewed as the standard model for each subgroup; H as relative weights of each sample belonging to each subgroup; e represents the model fitting residues, and r is the number of subgroups to be clustered (usually much smaller than m). Given r and V as input, the gNMF algorithm first randomly sets the initial value of W and H, and then iteratively updates W and H using multiplicative update rules pursuant to the below formulas (6 and 7):

$$H_{a\mu} \leftarrow H_{a\mu} \frac{\sum_i W_{ia} V_{i\mu} / (WH)_{i\mu}}{\sum_k W_{ka}} \quad (6)$$

$$W_{ia} \leftarrow W_{ia} \frac{\sum_\mu H_{a\mu} V_{i\mu} / (WH)_{i\mu}}{\sum_v H_{av}} \quad (7)$$

wherein α runs from 1 to r, μ runs from 1 to m, and i runs from 1 to n.

In previous applications of gNMF to cluster CGH data (See, Maher, E. A., et al., "Marked genomic differences characterize primary and secondary glioblastoma subtypes and identify two distinct molecular and clinical secondary glioblastoma entities," *Cancer Res*. 66:11502-13 (2006); Carrasco, D. R., et al., "High-resolution genomic profiles define distinct clinico-pathogenetic subgroups of multiple myeloma patients," *Cancer Cell*. 9:313-25 (2006)), the algorithm was stopped when the subgroup assignments of samples did not change after a pre-defined number of steps (e.g. 100). Based on tests with simulated data as well as actual CGH data, it was determined that this criterion might stop the procedure too early, suggesting that the results could potentially be further improved if the algorithm were allowed to run more steps. Therefore, the algorithm was modified so that after every 100 steps of multiplicative updating the divergence of the current model from the data is calculated pursuant to the below formula (1):

$$D(V \| WH) = \sum_{i=1}^{n} \sum_{j=1}^{m} \left( V_{ij} \log \frac{V_{ij}}{(WH)_{ij}} - V_{ij} + (WH)_{ij} \right) \quad (1)$$

wherein the $V_{ij}$ is the $i^{th}$ row and $i^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

The iterative algorithm will be stopped if the divergence does not decrease more than 0.001% of previous divergence calculated 100 steps ago. This modification significantly improved the accuracy of clustering at the cost of a higher computational complexity.

Since gNMF is a stochastic procedure, the algorithm may generate different outcomes when started from different initial values. To further improve the performance of the clustering algorithm, a new multiple initiation strategy was implemented. For each data set, (a) the gNMF algorithm was run 200 times following the above stop criterion; (b) the Pearson correlation coefficient matrix of H from the output of each of the 200 random gNMF runs was calculated; and (c) the correlation matrices over the 200 runs was averaged. The final clustering result was derived by running a hierarchical clustering algorithm using 1 minus the average correlation matrix as the distance matrix and cutting the dendrogram into r subgroups.

7. Model Selection Using Cophenetic Correlation and Bayesian Information Criterion (BIC).

The gNMF procedure described above in Section 6 was run with several possible r values (number of subgroups) chosen in the initial hierarchical clustering analysis. The Cophenetic correlation coefficient and Bayesian Information Criterion (BIC) were then used to select the best model.

Lognormal distribution is widely used to fit DNA copy numbers (See, Hodgson et al., *Nature*, 29:459 (2001)). To calculate the likelihood, it was assumed that samples in each cluster came from the same multi-lognormal distribution where the mean copy number of each segment follows a lognormal distribution. The correlation between segments was weak, so independence was assumed between segments in the calculation. The resulting log-likelihood was determined using the formula (12):

$$\ln L = \frac{1}{2}\ln(2\pi)\sum_{i=1}^{r}\sum_{j=1}^{n_i}\sum_{t=1}^{m}\frac{(y_{ijt}-\mu_{it})^2}{2\sigma_{it}^2}\ln(\sigma_{ij}) \quad (12)$$

wherein r is the number of clusters, n, is the number of samples in cluster i, m is the number of segments, $y_{ijt}$ is the log transformed copy number of the $t^{th}$ segment of the $j^{th}$ sample in the $i^{th}$ cluster, $\mu_{it}$ is the average of log transformed copy numbers of the $t^{th}$ segment in the $i^{th}$ cluster, and $\sigma_{it}$ is the standard deviation of log transformed copy numbers of the $t^{th}$ segment in the $i^{th}$ cluster. Then the number of parameters, k, in the specified model would be 2×r×m.

Both Cophenetic correlation coefficient and BIC were used as criterion to select the best gNMF model, and it was found these two criteria often selected the same model.

8. 10-fold Stability Test of Clustering Stability.

A 10-fold stability test procedure was developed to assess the stability of the clustering results. After running gNMF on a data set and assigning samples to clusters, 10% of samples were randomly left out and the same procedure was applied on the remaining 90% of samples. The number of samples that were assigned to a different subgroup by this permutation was calculated. This "leave-out" test was repeated 200 times to derive an error rate, which represented the stability of the clustering result with respect to permutation of samples. The stability of hierarchical clustering was also assessed using the same procedure for the same data sets and it was found that it was always much higher than that of gNMF clustering.

In the following examples 3-4, the methods in this Example 1 are applied to two types of cancer, namely, non-small cell lung carcinoma and colorectal cancer. The step numbers used in the examples correspond to those steps described above in this Example 1.

EXAMPLE 2

A Second General Methodology and Algorithm for Assembling Panels of Cell Lines and/or Xenografts 1. Acquisition of CGH Data for Cell Lines and Tumors The CGH data for cell lines and tumors were downloaded from public databases. The original data from the public databases was generated using Affymetrix 250K Sty arrays following the manufacturer's instructions (See, *GeneChip® Mapping 500K Assay Manual* PN 701930 Rev. 3, Affymetrix (2005-2006)).

2. Copy Number Determination and Detection of Copy Number Alterations.

Partek® Genomic Suite™ software (version 6.08.0103) was used for low-level processing of the data to determine the copy numbers of each locus and define regions of copy number alteration. CEL files containing signals for all SNPs probes were loaded into the software, and copy numbers were calculated by comparing the signal intensities for tumor or cell line samples to those for a reference set of 90 normal female tissue samples, corrected to a baseline of 2. The reference set can also consist of other sets of normal samples, or paired normal tissues from the same patients of the tumor samples, measured by the same microarray platform.

The resulting probe-level copy number data were segmented and the copy number alteration regions were detected in each sample. Specifically, probe-level copy numbers were segmented into regions using the following control parameters: (i) a region must contain at least 100 probes, (ii) the p-value comparing the mean copy number of the region versus the adjacent regions must be less than 0.00001, and (iii) the signal/noise ratio of the transition must be greater than 0.1. Then the copy number alteration regions were detected when the mean copy numbers in these regions were statistically less than 1.65 (deletion) or greater than 2.65 (gain) with P values below 0.01.

3. Data Quality Control.

Tumor samples may contain a significant percentage of normal cells, which will dilute the signal of copy number alteration. A machine learning algorithm was developed to capture the difference between copy number patterns of tumor and normal samples and then used it to identify and eliminate normal contaminated samples from further analyses. First, a subset of samples with the highest number of copy number alteration regions and a set of normal samples were selected. These two groups of samples were used as a training set to train a machine learning algorithm (Random Forests (See, Breiman, L., "Random Forests," *Machine Learning*, 45(1):5-32 (2001))) to classify normal and tumor samples by tuning the parameters to best represent the difference between tumor and normal samples. The trained classifier was applied to the rest of samples to assign a score to each sample that represented the probability of it being contaminated by normal cells. Samples with normal contamination probability over 50% were excluded from clustering analysis.

4. Data Smoothing and Dimension Reduction.

Because of the high density of copy number data obtained by SNPs microarrays and the significant amount of noise, the copy number data need to be smoothed to decrease the noise level and reduce the dimensionality and complexity of the clustering analysis. After detecting significantly gained or deleted regions in each sample, the adjacent regions were merged if they had similar copy number changes and the distance between them was less than 500 kb. The DNA segments were formed by using the union of break points from all samples in a data set. The average copy number of probes within each segment was used for further analysis. This step allowed for a clearer resolution of DNA gains and deletions in a high-throughput analysis.

5. Pilot Clustering Analysis Using Hierarchical Clustering to Determine the Possible Number of Subgroups.

Although widely used in many applications, hierarchical clustering has a number of drawbacks for genomic studies. First, it cannot consistently and objectively estimate the number of subgroups in a dataset. Second, hierarchical clustering patterns can be unstable. Specifically, a clustering pattern could change dramatically when a small number of samples is added to or deleted from a dataset. Additionally, in this analysis, a much higher error rate was observed when the 10-fold stability test result of hierarchical clustering was compared with that for gNMF (See, Section 8 below).

Nevertheless, hierarchical clustering can serve as a useful tool to quickly derive an overview of the relative similarity between samples and provide a rough estimate of the possible number of subgroups that exist in the data. For each data set, the tumor and cell line CGH data was hierarchically clustered using Pearson linear dissimilarity. The hierarchical clustering patterns were plotted and visually inspected to derive a range of possible numbers of subgroups in the dataset. These numbers were then used as input in the clustering analysis using genomic Non-negative Matrix Factorization (See Section 6 below).

6. gNMF Clustering of the Tumor and Cell Line CGH Data.

NMF was first adopted in genomics for analysis of gene expression data (See, Brunet, J. P., et al., Metagenes and molecular pattern discovery using matrix factorization. *Proc Natl Acad Sci USA.* 101:4164-9 (2004)). The methodology was then adapted for use in the analysis of gene copy number data (See, Maher, E. A., et al., "Marked genomic differences characterize primary and secondary glioblastoma subtypes and identify two distinct molecular and clinical secondary glioblastoma entities," *Cancer Res.* 66:11502-13 (2006); Carrasco, D. R., et al., "High-resolution genomic profiles define distinct clinico-pathogenetic subgroups of multiple myeloma patients," *Cancer Cell.* 9:313-25 (2006)). Given a n×m matrix V of smoothed copy number data for a set of samples (namely, in the data set), where n is the number of segments and m is the number of samples, the gNMF algorithm factorizes the matrix V into an n×r matrix W and a r×m matrix H as shown in the below formula (5):

$$V = W*H + e \quad (5).$$

In the above formula (5), W can be viewed as the standard model for each subgroup; H as relative weights of each sample belonging to each subgroup; e represents the model fitting residues, and r is the number of subgroups to be clustered (usually much smaller than m). Given r and V as input, the gNMF algorithm first randomly sets the initial value of W and H, and then iteratively updates W and H using multiplicative update rules pursuant to the below formulas (6 and 7):

$$H_{a\mu} \leftarrow H_{a\mu} \frac{\sum_i W_{ia} V_{i\mu}/(WH)_{i\mu}}{\sum_k W_{ka}} \quad (6)$$

$$W_{ia} \leftarrow W_{ia} \frac{\sum_\mu H_{a\mu} V_{i\mu}/(WH)_{i\mu}}{\sum_v H_{av}} \quad (7)$$

wherein α runs from 1 to r, μ runs from 1 to m, and i runs from 1 to n.

In previous applications of gNMF to cluster CGH data (See, Maher, E. A., et al., "Marked genomic differences characterize primary and secondary glioblastoma subtypes and identify two distinct molecular and clinical secondary glioblastoma entities," *Cancer Res.* 66:11502-13 (2006); Carrasco, D. R., et al., "High-resolution genomic profiles define distinct clinico-pathogenetic subgroups of multiple myeloma patients," *Cancer Cell.* 9:313-25 (2006)), the algorithm was stopped when the subgroup assignments of samples did not change after a pre-defined number of steps (e.g. 100). Based on tests with simulated data as well as actual CGH data, it was determined that this criterion might stop the procedure too early, suggesting that the results could potentially be further improved if the algorithm were allowed to run more steps. Therefore, the algorithm was modified so that after every 100 steps of multiplicative updating the divergence of the current model from the data is calculated pursuant to the below formula (1):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (1)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of segments in the data set, and j runs from 1 to m and m is the number of samples in the data set.

The iterative algorithm will be stopped if the divergence does not decrease more than 0.001% of previous divergence calculated 100 steps ago. This modification significantly improved the accuracy of clustering at the cost of a higher computational complexity.

Since gNMF is a stochastic procedure, the algorithm may generate different outcomes when started from different initial values. To further improve the performance of the clustering algorithm, a new multiple initiation strategy was implemented. For each data set, (a) the gNMF algorithm was run 200 times following the above stop criterion; (b) the Pearson correlation coefficient matrix of H from the output of each of the 200 random gNMF runs was calculated; and (c) the correlation matrices over the 200 runs was averaged. The final clustering result was derived by running a hierarchical clustering algorithm using 1 minus the average correlation matrix as the distance matrix and cutting the dendrogram into r subgroups.

7. Model Selection Using Bayesian Information Criterion (BIC).

The gNMF procedure described above in Section 6 was run with several possible r values (number of subgroups) chosen in the initial hierarchical clustering analysis. Bayesian Information Criterion (BIC) was then used to select the best model.

Lognormal distribution is widely used to fit DNA copy numbers (See, Hodgson et al., *Nature,* 29:459 (2001)). To calculate the likelihood, it was assumed that samples in each cluster came from the same multi-lognormal distribution where the mean copy number of each segment follows a lognormal distribution. The correlation between segments was weak, so independence was assumed between segments in the calculation. The resulting log-likelihood was determined using the below formula (12):

$$\ln L = \frac{1}{2}\ln(2\pi)\sum_{i=1}^{r}\sum_{j=1}^{n_i}\sum_{t=1}^{m}\frac{(y_{ijt} - \mu_{it})^2}{2\sigma_{it}^2}\ln(\sigma_{ij}) \quad (12)$$

wherein r is the number of clusters, $n_i$ is the number of samples in cluster i, m is the number of segments, $y_{ijt}$ is the log transformed copy number of the $t^{th}$ segment of the $j^{th}$ sample in the $i^{th}$ cluster, $\mu_{it}$ is the average of log transformed copy numbers of the $t^{th}$ segment in the $i^{th}$ cluster, and $\sigma_{it}$ is the standard deviation of log transformed copy numbers of the $t^{th}$ segment in the $i^{th}$ cluster. Then the number of parameters, k, in the specified model would be 2×r×m.

BIC were used as criterion to select the best model in the unsupervised clustering.

8. 10-Fold Stability Test of Clustering Stability.

A 10-fold stability test procedure was developed to assess the stability of the clustering results. After running gNMF on a data set and assigning samples to clusters, 10% of samples were randomly left out and the same procedure was applied on the remaining 90% of samples. The number of samples that were assigned to a different subgroup by this permutation was calculated. This "leave-out" test was repeated 200 times to derive an error rate, which represented the stability of the clustering result with respect to permutation of samples. The stability of hierarchical clustering was also assessed using the same procedure for the same data sets and it was found that it was always much higher than that of gNMF clustering.

In the following example 5, the methods in this Example 2 are applied to melanoma. The step numbers used in the examples correspond to those steps described above in this Example 2.

EXAMPLE 3

Classification of Non-Small Cell Lung Carcinoma (NSCLC) Tumors and Cell Lines Steps 1-2. DNA extraction and hybridization and copy number determination and detection of copy number alterations. We used 57 cell lines and 245 tumor samples in this study (all cell lines are listed in Table A and all tumor samples are listed in Table 1). The NSCLC tumor and cell line samples were processed, and the data were processed as described in Example 1. A total of 11419 segments with a significantly altered copy number were detected.

TABLE 1

| ID | Source |
|---|---|
| NSCLC21 | Caprion Proteomics, Montreal, Quebec |
| NSCLC22 | Caprion Proteomics, Montreal, Quebec |
| NSCLC23 | Caprion Proteomics, Montreal, Quebec |
| NSCLC24 | Caprion Proteomics, Montreal, Quebec |
| NSCLC25 | Caprion Proteomics, Montreal, Quebec |
| NSCLC26 | Caprion Proteomics, Montreal, Quebec |
| NSCLC27 | Caprion Proteomics, Montreal, Quebec |
| NSCLC28 | Caprion Proteomics, Montreal, Quebec |
| NSCLC29 | Caprion Proteomics, Montreal, Quebec |
| NSCLC30 | Caprion Proteomics, Montreal, Quebec |
| NSCLC31 | Caprion Proteomics, Montreal, Quebec |
| NSCLC33 | Caprion Proteomics, Montreal, Quebec |
| NSCLC34 | Caprion Proteomics, Montreal, Quebec |
| NSCLC35 | Caprion Proteomics, Montreal, Quebec |
| NSCLC36 | Caprion Proteomics, Montreal, Quebec |
| NSCLC37 | Caprion Proteomics, Montreal, Quebec |
| NSCLC38 | Caprion Proteomics, Montreal, Quebec |
| NSCLC41 | Caprion Proteomics, Montreal, Quebec |
| NSCLC42 | Caprion Proteomics, Montreal, Quebec |
| NSCLC43 | Caprion Proteomics, Montreal, Quebec |
| NSCLC44 | Caprion Proteomics, Montreal, Quebec |
| NSCLC45 | Caprion Proteomics, Montreal, Quebec |
| NSCLC46 | Caprion Proteomics, Montreal, Quebec |
| NSCLC47 | Caprion Proteomics, Montreal, Quebec |
| NSCLC49 | Caprion Proteomics, Montreal, Quebec |
| NSCLC50 | Caprion Proteomics, Montreal, Quebec |
| NSCLC52 | Caprion Proteomics, Montreal, Quebec |
| NSCLC53 | Caprion Proteomics, Montreal, Quebec |
| NSCLC55 | Caprion Proteomics, Montreal, Quebec |
| NSCLC58 | Caprion Proteomics, Montreal, Quebec |
| NSCLC60 | Caprion Proteomics, Montreal, Quebec |
| NSCLC65 | Caprion Proteomics, Montreal, Quebec |
| NSCLC66 | Caprion Proteomics, Montreal, Quebec |
| NSCLC67 | Caprion Proteomics, Montreal, Quebec |
| NSCLC69 | Caprion Proteomics, Montreal, Quebec |
| NSCLC70 | Caprion Proteomics, Montreal, Quebec |
| NSCLC71 | Caprion Proteomics, Montreal, Quebec |
| NSCLC72 | Caprion Proteomics, Montreal, Quebec |
| NSCLC75 | Caprion Proteomics, Montreal, Quebec |
| NSCLC76 | Caprion Proteomics, Montreal, Quebec |
| NSCLC79 | Caprion Proteomics, Montreal, Quebec |
| NSCLC82 | Caprion Proteomics, Montreal, Quebec |
| NSCLC85 | Caprion Proteomics, Montreal, Quebec |
| NSCLC299 | Data obtained from the Dana-Farber Cancer Institute |

TABLE 1-continued

| ID | Source |
|---|---|
| NSCLC300 | Data obtained from the Dana-Farber Cancer Institute |
| NSCLC301 | Data obtained from the Dana-Farber Cancer Institute |
| NSCLC303 | Data obtained from the Dana-Farber Cancer Institute |
| NSCLC305 | Data obtained from the Dana-Farber Cancer Institute |
| NSCLC307 | Data obtained from the Dana-Farber Cancer Institute |
| NSCLC308 | Data obtained from the Dana-Farber Cancer Institute |
| NSCLC309 | Data obtained from the Dana-Farber Cancer Institute |
| NSCLC311 | Data obtained from the Dana-Farber Cancer Institute |
| NSCLC312 | Data obtained from the Dana-Farber Cancer Institute |
| NSCLC314 | Data obtained from the Dana-Farber Cancer Institute |
| NSCLC315 | Data obtained from the Dana-Farber Cancer Institute |
| NSCLC316 | Data obtained from the Dana-Farber Cancer Institute |
| NSCLC317 | Data obtained from the Dana-Farber Cancer Institute |
| NSCLC318 | Data obtained from the Dana-Farber Cancer Institute |
| NSCLC319 | Data obtained from the Dana-Farber Cancer Institute |
| NSCLC320 | Data obtained from the Dana-Farber Cancer Institute |
| NSCLC322 | Data obtained from the Dana-Farber Cancer Institute |
| NSCLC323 | Data obtained from the Dana-Farber Cancer Institute |
| NSCLC325 | Data obtained from the Dana-Farber Cancer Institute |
| NSCLC327 | Data obtained from the Dana-Farber Cancer Institute |
| NSCLC328 | Data obtained from the Dana-Farber Cancer Institute |
| NSCLC330 | Data obtained from the Dana-Farber Cancer Institute |
| NSCLC332 | Data obtained from the Dana-Farber Cancer Institute |
| NSCLC333 | Data obtained from the Dana-Farber Cancer Institute |
| NSCLC334 | Data obtained from the Dana-Farber Cancer Institute |
| NSCLC335 | Data obtained from the Dana-Farber Cancer Institute |
| NSCLC336 | Data obtained from the Dana-Farber Cancer Institute |
| NSCLC337 | Data obtained from the Dana-Farber Cancer Institute |
| NSCLC338 | Data obtained from the Dana-Farber Cancer Institute |
| NSCLC339 | Data obtained from the Dana-Farber Cancer Institute |
| NSCLC340 | Data obtained from the Dana-Farber Cancer Institute |
| NSCLC341 | Data obtained from the Dana-Farber Cancer Institute |
| NSCLC342 | Data obtained from the Dana-Farber Cancer Institute |
| NSCLC344 | Data obtained from the Dana-Farber Cancer Institute |
| NSCLC345 | Data obtained from the Dana-Farber Cancer Institute |
| NSCLC346 | Data obtained from the Dana-Farber Cancer Institute |
| NSCLC347 | Data obtained from the Dana-Farber Cancer Institute |
| NSCLC1 | ProteoGenex, Culver City, CA |
| NSCLC10 | ProteoGenex, Culver City, CA |
| NSCLC11 | ProteoGenex, Culver City, CA |
| NSCLC12 | ProteoGenex, Culver City, CA |

TABLE 1-continued

| ID | Source |
|---|---|
| NSCLC13 | ProteoGenex, Culver City, CA |
| NSCLC14 | ProteoGenex, Culver City, CA |
| NSCLC15 | ProteoGenex, Culver City, CA |
| NSCLC17 | ProteoGenex, Culver City, CA |
| NSCLC18 | ProteoGenex, Culver City, CA |
| NSCLC19 | ProteoGenex, Culver City, CA |
| NSCLC2 | ProteoGenex, Culver City, CA |
| NSCLC20 | ProteoGenex, Culver City, CA |
| NSCLC4 | ProteoGenex, Culver City, CA |
| NSCLC5 | ProteoGenex, Culver City, CA |
| NSCLC7 | ProteoGenex, Culver City, CA |
| NSCLC8 | ProteoGenex, Culver City, CA |
| NSCLC9 | ProteoGenex, Culver City, CA |
| NSCLC100 | Rush Presbyterian, Chicago, IL (Dr. Coon) |
| NSCLC101 | Rush Presbyterian, Chicago, IL (Dr. Coon) |
| NSCLC103 | Rush Presbyterian, Chicago, IL (Dr. Coon) |
| NSCLC104 | Rush Presbyterian, Chicago, IL (Dr. Coon) |
| NSCLC105 | Rush Presbyterian, Chicago, IL (Dr. Coon) |
| NSCLC106 | Rush Presbyterian, Chicago, IL (Dr. Coon) |
| NSCLC108 | Rush Presbyterian, Chicago, IL (Dr. Coon) |
| NSCLC109 | Rush Presbyterian, Chicago, IL (Dr. Coon) |
| NSCLC110 | Rush Presbyterian, Chicago, IL (Dr. Coon) |
| NSCLC111 | Rush Presbyterian, Chicago, IL (Dr. Coon) |
| NSCLC113 | Rush Presbyterian, Chicago, IL (Dr. Coon) |
| NSCLC115 | Rush Presbyterian, Chicago, IL (Dr. Coon) |
| NSCLC116 | Rush Presbyterian, Chicago, IL (Dr. Coon) |
| NSCLC117 | Rush Presbyterian, Chicago, IL (Dr. Coon) |
| NSCLC118 | Rush Presbyterian, Chicago, IL (Dr. Coon) |
| NSCLC119 | Rush Presbyterian, Chicago, IL (Dr. Coon) |
| NSCLC120 | Rush Presbyterian, Chicago, IL (Dr. Coon) |
| NSCLC121 | Rush Presbyterian, Chicago, IL (Dr. Coon) |
| NSCLC122 | Rush Presbyterian, Chicago, IL (Dr. Coon) |
| NSCLC123 | Rush Presbyterian, Chicago, IL (Dr. Coon) |
| NSCLC125 | Rush Presbyterian, Chicago, IL (Dr. Coon) |
| NSCLC126 | Rush Presbyterian, Chicago, IL (Dr. Coon) |
| NSCLC127 | Rush Presbyterian, Chicago, IL (Dr. Coon) |
| NSCLC128 | Rush Presbyterian, Chicago, IL (Dr. Coon) |
| NSCLC129 | Rush Presbyterian, Chicago, IL (Dr. Coon) |
| NSCLC130 | Rush Presbyterian, Chicago, IL (Dr. Coon) |
| NSCLC132 | Rush Presbyterian, Chicago, IL (Dr. Coon) |
| NSCLC133 | Rush Presbyterian, Chicago, IL (Dr. Coon) |
| NSCLC134 | Rush Presbyterian, Chicago, IL (Dr. Coon) |
| NSCLC135 | Rush Presbyterian, Chicago, IL (Dr. Coon) |
| NSCLC136 | Rush Presbyterian, Chicago, IL (Dr. Coon) |
| NSCLC137 | Rush Presbyterian, Chicago, IL (Dr. Coon) |
| NSCLC138 | Rush Presbyterian, Chicago, IL (Dr. Coon) |
| NSCLC139 | Rush Presbyterian, Chicago, IL (Dr. Coon) |
| NSCLC143 | Rush Presbyterian, Chicago, IL (Dr. Coon) |
| NSCLC144 | Rush Presbyterian, Chicago, IL (Dr. Coon) |
| NSCLC145 | Rush Presbyterian, Chicago, IL (Dr. Coon) |
| NSCLC146 | Rush Presbyterian, Chicago, IL (Dr. Coon) |
| NSCLC150 | Rush Presbyterian, Chicago, IL (Dr. Coon) |
| NSCLC151 | Rush Presbyterian, Chicago, IL (Dr. Coon) |
| NSCLC153 | Rush Presbyterian, Chicago, IL (Dr. Coon) |
| NSCLC155 | Rush Presbyterian, Chicago, IL (Dr. Coon) |
| NSCLC156 | Rush Presbyterian, Chicago, IL (Dr. Coon) |
| NSCLC157 | Rush Presbyterian, Chicago, IL (Dr. Coon) |
| NSCLC158 | Rush Presbyterian, Chicago, IL (Dr. Coon) |
| NSCLC159 | Rush Presbyterian, Chicago, IL (Dr. Coon) |
| NSCLC160 | Rush Presbyterian, Chicago, IL (Dr. Coon) |
| NSCLC162 | Rush Presbyterian, Chicago, IL (Dr. Coon) |
| NSCLC164 | Rush Presbyterian, Chicago, IL (Dr. Coon) |
| NSCLC165 | Rush Presbyterian, Chicago, IL (Dr. Coon) |
| NSCLC166 | Rush Presbyterian, Chicago, IL (Dr. Coon) |
| NSCLC167 | Rush Presbyterian, Chicago, IL (Dr. Coon) |
| NSCLC168 | Rush Presbyterian, Chicago, IL (Dr. Coon) |
| NSCLC171 | Rush Presbyterian, Chicago, IL (Dr. Coon) |
| NSCLC172 | Rush Presbyterian, Chicago, IL (Dr. Coon) |
| NSCLC173 | Rush Presbyterian, Chicago, IL (Dr. Coon) |
| NSCLC174 | Rush Presbyterian, Chicago, IL (Dr. Coon) |
| NSCLC175 | Rush Presbyterian, Chicago, IL (Dr. Coon) |
| NSCLC176 | Rush Presbyterian, Chicago, IL (Dr. Coon) |
| NSCLC177 | Rush Presbyterian, Chicago, IL (Dr. Coon) |
| NSCLC178 | Rush Presbyterian, Chicago, IL (Dr. Coon) |
| NSCLC179 | Rush Presbyterian, Chicago, IL (Dr. Coon) |
| NSCLC180 | Rush Presbyterian, Chicago, IL (Dr. Coon) |
| NSCLC1h81 | Rush Presbyterian, Chicago, IL (Dr. Coon) |
| NSCLC182 | Rush Presbyterian, Chicago, IL (Dr. Coon) |
| NSCLC184 | Rush Presbyterian, Chicago, IL (Dr. Coon) |
| NSCLC185 | Rush Presbyterian, Chicago, IL (Dr. Coon) |
| NSCLC187 | Rush Presbyterian, Chicago, IL (Dr. Coon) |
| NSCLC188 | Rush Presbyterian, Chicago, IL (Dr. Coon) |
| NSCLC189 | Rush Presbyterian, Chicago, IL (Dr. Coon) |
| NSCLC191 | Rush Presbyterian, Chicago, IL (Dr. Coon) |
| NSCLC192 | Rush Presbyterian, Chicago, IL (Dr. Coon) |
| NSCLC194 | Rush Presbyterian, Chicago, IL (Dr. Coon) |
| NSCLC195 | Rush Presbyterian, Chicago, IL (Dr. Coon) |
| NSCLC196 | Rush Presbyterian, Chicago, IL (Dr. Coon) |
| NSCLC198 | Rush Presbyterian, Chicago, IL (Dr. Coon) |
| NSCLC199 | Rush Presbyterian, Chicago, IL (Dr. Coon) |
| NSCLC201 | Rush Presbyterian, Chicago, IL (Dr. Coon) |
| NSCLC203 | Rush Presbyterian, Chicago, IL (Dr. Coon) |
| NSCLC206 | Rush Presbyterian, Chicago, IL (Dr. Coon) |
| NSCLC208 | Rush Presbyterian, Chicago, IL (Dr. Coon) |
| NSCLC209 | Rush Presbyterian, Chicago, IL (Dr. Coon) |
| NSCLC210 | Rush Presbyterian, Chicago, IL (Dr. Coon) |
| NSCLC214 | Rush Presbyterian, Chicago, IL (Dr. Coon) |
| NSCLC215 | Rush Presbyterian, Chicago, IL (Dr. Coon) |
| NSCLC216 | Rush Presbyterian, Chicago, IL (Dr. Coon) |
| NSCLC217 | Rush Presbyterian, Chicago, IL (Dr. Coon) |
| NSCLC218 | Rush Presbyterian, Chicago, IL (Dr. Coon) |
| NSCLC221 | Rush Presbyterian, Chicago, IL (Dr. Coon) |
| NSCLC222 | Rush Presbyterian, Chicago, IL (Dr. Coon) |
| NSCLC223 | Rush Presbyterian, Chicago, IL (Dr. Coon) |
| NSCLC225 | Rush Presbyterian, Chicago, IL (Dr. Coon) |
| NSCLC227 | Rush Presbyterian, Chicago, IL (Dr. Coon) |
| NSCLC228 | Rush Presbyterian, Chicago, IL (Dr. Coon) |
| NSCLC230 | Rush Presbyterian, Chicago, IL (Dr. Coon) |
| NSCLC231 | Rush Presbyterian, Chicago, IL (Dr. Coon) |
| NSCLC232 | Rush Presbyterian, Chicago, IL (Dr. Coon) |
| NSCLC233 | Rush Presbyterian, Chicago, IL (Dr. Coon) |
| NSCLC234 | Rush Presbyterian, Chicago, IL (Dr. Coon) |
| NSCLC236 | Rush Presbyterian, Chicago, IL (Dr. Coon) |
| NSCLC237 | Rush Presbyterian, Chicago, IL (Dr. Coon) |
| NSCLC238 | Rush Presbyterian, Chicago, IL (Dr. Coon) |
| NSCLC239 | Rush Presbyterian, Chicago, IL (Dr. Coon) |
| NSCLC242 | Rush Presbyterian, Chicago, IL (Dr. Coon) |
| NSCLC243 | Rush Presbyterian, Chicago, IL (Dr. Coon) |
| NSCLC246 | Rush Presbyterian, Chicago, IL (Dr. Coon) |
| NSCLC249 | Rush Presbyterian, Chicago, IL (Dr. Coon) |
| NSCLC250 | Rush Presbyterian, Chicago, IL (Dr. Coon) |
| NSCLC251 | Rush Presbyterian, Chicago, IL (Dr. Coon) |
| NSCLC252 | Rush Presbyterian, Chicago, IL (Dr. Coon) |
| NSCLC253 | Rush Presbyterian, Chicago, IL (Dr. Coon) |
| NSCLC254 | Rush Presbyterian, Chicago, IL (Dr. Coon) |
| NSCLC255 | Rush Presbyterian, Chicago, IL (Dr. Coon) |
| NSCLC256 | Rush Presbyterian, Chicago, IL (Dr. Coon) |
| NSCLC258 | Rush Presbyterian, Chicago, IL (Dr. Coon) |
| NSCLC259 | Rush Presbyterian, Chicago, IL (Dr. Coon) |
| NSCLC260 | Rush Presbyterian, Chicago, IL (Dr. Coon) |
| NSCLC261 | Rush Presbyterian, Chicago, IL (Dr. Coon) |
| NSCLC265 | Rush Presbyterian, Chicago, IL (Dr. Coon) |
| NSCLC266 | Rush Presbyterian, Chicago, IL (Dr. Coon) |
| NSCLC269 | Rush Presbyterian, Chicago, IL (Dr. Coon) |
| NSCLC270 | Rush Presbyterian, Chicago, IL (Dr. Coon) |
| NSCLC271 | Rush Presbyterian, Chicago, IL (Dr. Coon) |
| NSCLC272 | Rush Presbyterian, Chicago, IL (Dr. Coon) |
| NSCLC273 | Rush Presbyterian, Chicago, IL (Dr. Coon) |
| NSCLC274 | Rush Presbyterian, Chicago, IL (Dr. Coon) |
| NSCLC275 | Rush Presbyterian, Chicago, IL (Dr. Coon) |
| NSCLC276 | Rush Presbyterian, Chicago, IL (Dr. Coon) |
| NSCLC277 | Rush Presbyterian, Chicago, IL (Dr. Coon) |
| NSCLC278 | Rush Presbyterian, Chicago, IL (Dr. Coon) |
| NSCLC280 | Rush Presbyterian, Chicago, IL (Dr. Coon) |
| NSCLC282 | Rush Presbyterian, Chicago, IL (Dr. Coon) |
| NSCLC283 | Rush Presbyterian, Chicago, IL (Dr. Coon) |
| NSCLC284 | Rush Presbyterian, Chicago, IL (Dr. Coon) |
| NSCLC286 | Rush Presbyterian, Chicago, IL (Dr. Coon) |
| NSCLC288 | Rush Presbyterian, Chicago, IL (Dr. Coon) |
| NSCLC290 | Rush Presbyterian, Chicago, IL (Dr. Coon) |
| NSCLC291 | Rush Presbyterian, Chicago, IL (Dr. Coon) |
| NSCLC292 | Rush Presbyterian, Chicago, IL (Dr. Coon) |
| NSCLC294 | Rush Presbyterian, Chicago, IL (Dr. Coon) |
| NSCLC295 | Rush Presbyterian, Chicago, IL (Dr. Coon) |
| NSCLC296 | Rush Presbyterian, Chicago, IL (Dr. Coon) |
| NSCLC298 | Rush Presbyterian, Chicago, IL (Dr. Coon) |

TABLE 1-continued

| ID | Source |
|---|---|
| NSCLC96 | Rush Presbyterian, Chicago, IL (Dr. Coon) |
| NSCLC97 | Rush Presbyterian, Chicago, IL (Dr. Coon) |
| NSCLC98 | Rush Presbyterian, Chicago, IL (Dr. Coon) |
| NSCLC99 | Rush Presbyterian, Chicago, IL (Dr. Coon) |

Step 3. Data quality control. We applied the data quality control procedure described in Example 1 to our NSCLC CGH data. No tumor samples were found to be significantly contaminated by normal cells. Therefore, we used all the samples in our analysis.

Step 4. Data smoothing and dimension reduction. Using the method described in Example 1, we reduced the dimensionality of the CGH data to 8172 segments and used this data as the data set (V) in our following analyses.

Figure 2:
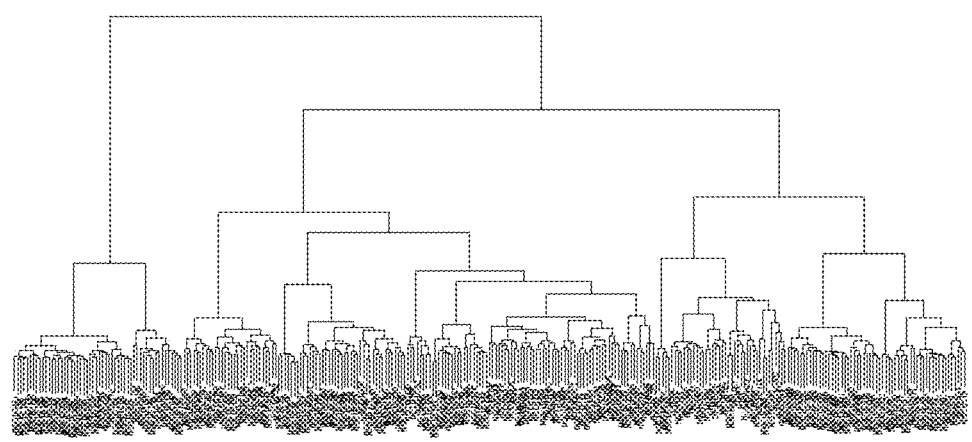
FIG. 2 shows the hierarchical clustering used to generate a dendrogram of a non-small cell lung carcinoma (NSCLC) data set in order to derive the possible number of clusters as described in Example 3.

Step 5. Initial clustering analysis. Hierarchical clustering was used as initial analysis on our NSCLC data set to estimate the number of clusters. The dendrogram of the clustering is shown in FIG. 2. Visual inspection of the dendrogram suggested the existence of 3-8 major clusters in the data set.

Step 6. Classification of NSCLC tumors and cell lines using gNMF. The gNMF algorithm was used as described in Example 1 to classify the tumor and cell line CGH data, using cluster numbers in the range of 3-8. With each cluster number, the gNMF algorithm was run 200 times using the stop criterion developed (See, Example 1). Classification models were then derived by hierarchical clustering on 1 minus the average of correlation matrix of H.

Figure 3:
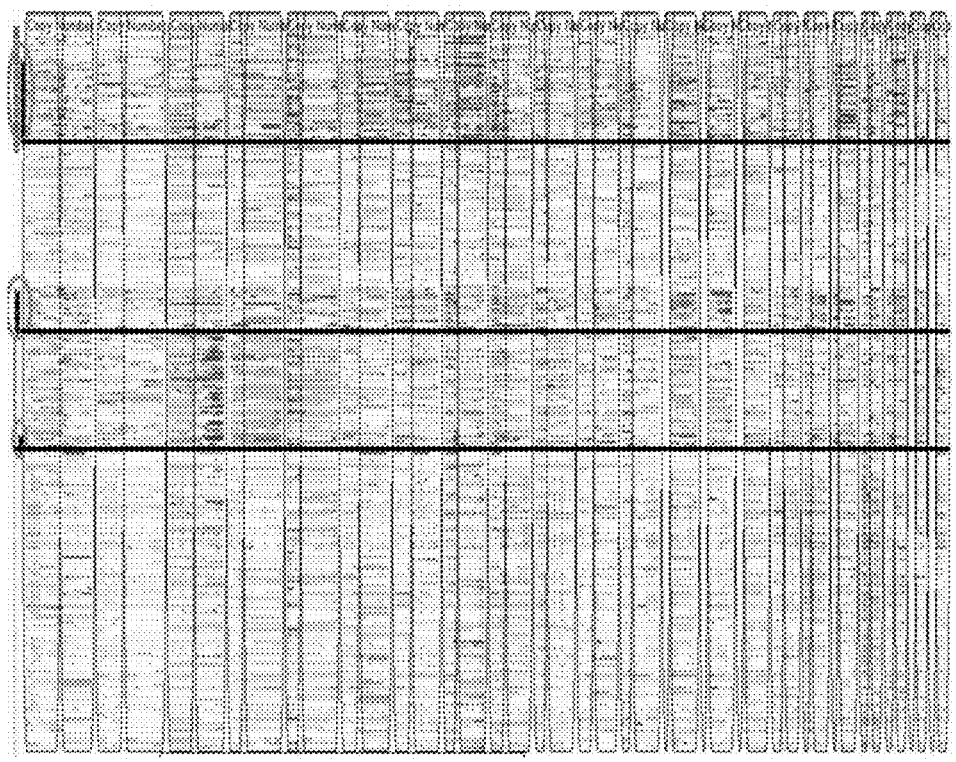
FIG. 3 shows a heatmap of NSCLC tumor and cell line CGH data from Example 3 classified by genomic Non-negative Matrix Factorization (gNMF) into 4 clusters. Each row represents a sample and each column represents a SNPs locus; red, white and blue colors indicate high, normal and low copy numbers, respectively; horizontal black lines separate different clusters; vertical spaces separate chromosomes 1 to 22; cell lines are highlighted by green circles.

Step 7. Model selection using Cophenetic correlation and BIC. We calculated the Cophenetic correlation and BIC as described in Example 1 for the gNMF models developed in step 6. The results are shown below in Table 2. In this table, r denotes the number of clusters in each model. From Table 2, we found that the model with 4 clusters has the smallest BIC, and that between cluster numbers 4 and 5, the Cophenetic correlation shows the greatest decrease. Therefore, 4 clusters is the best choice for this data set. The heatmap of the gNMF output with 4 clusters is shown in FIG. 3.

TABLE 2

| r | Cophenetic correlation | BIC |
|---|---|---|
| 3 | 0.8031 | 1032670 |
| 4 | 0.7664 | 992443 |
| 5 | 0.7103 | 1249580 |
| 6 | 0.7166 | 1301055 |
| 7 | 0.7040 | 1301808 |
| 8 | 0.7109 | 1202876 |

Step 8. The 10-fold test of clustering stability. We applied the 10-fold stability test described in Example 1 to the gNMF model with 4 clusters. The error rate was 14.24%. As a comparison, we also cut the hierarchical clustering dendrogram derived using the smoothed copy number data in step 5 into 3-8 clusters, and tested the stability of the clusters using the same 10-fold test. The error rates were 19.45%-25.65%, much higher than that of the gNMF model.

EXAMPLE 4

Classification of Colorectal Cancer (CRC) Tumors and Cell Lines

Steps 1-2. DNA extraction and hybridization and copy number determination and detection of copy number alterations. We used 35 cell lines and 144 tumor samples in this study (all cell lines are listed in Table B and all tumor samples are shown below in Table 3). The CRC tumor and cell line samples were prepared, and the data were processed as described in Example 1. A total of 5240 segments with a significantly altered copy number were detected.

TABLE 3

| ID | Source |
|---|---|
| CRC35 | Asterand, Detroit, MI |
| CRC36 | Asterand, Detroit, MI |
| CRC37 | Asterand, Detroit, MI |
| CRC38 | Asterand, Detroit, MI |
| CRC39 | Asterand, Detroit, MI |
| CRC40 | Asterand, Detroit, MI |
| CRC41 | Asterand, Detroit, MI |
| CRC42 | Asterand, Detroit, MI |
| CRC43 | Asterand, Detroit, MI |
| CRC44 | Asterand, Detroit, MI |
| CRC45 | Asterand, Detroit, MI |
| CRC46 | Asterand, Detroit, MI |
| CRC47 | Asterand, Detroit, MI |
| CRC48 | Asterand, Detroit, MI |
| CRC49 | Asterand, Detroit, MI |
| CRC50 | Asterand, Detroit, MI |
| CRC51 | Asterand, Detroit, MI |
| CRC52 | Asterand, Detroit, MI |
| CRC53 | Asterand, Detroit, MI |
| CRC54 | Asterand, Detroit, MI |
| CRC55 | Asterand, Detroit, MI |
| CRC56 | Asterand, Detroit, MI |
| CRC57 | Asterand, Detroit, MI |
| CRC58 | Asterand, Detroit, MI |
| CRC59 | Asterand, Detroit, MI |
| CRC61 | Asterand, Detroit, MI |
| CRC62 | Asterand, Detroit, MI |
| CRC63 | Asterand, Detroit, MI |
| CRC65 | Asterand, Detroit, MI |
| CRC66 | Asterand, Detroit, MI |
| CRC67 | Asterand, Detroit, MI |
| CRC68 | Asterand, Detroit, MI |
| CRC69 | Asterand, Detroit, MI |
| CRC70 | Asterand, Detroit, MI |
| CRC71 | Asterand, Detroit, MI |
| CRC72 | Asterand, Detroit, MI |
| CRC73 | Asterand, Detroit, MI |
| CRC74 | Asterand, Detroit, MI |
| CRC75 | Asterand, Detroit, MI |
| CRC76 | Asterand, Detroit, MI |
| CRC77 | Asterand, Detroit, MI |
| CRC78 | Asterand, Detroit, MI |
| CRC79 | Asterand, Detroit, MI |
| CRC80 | Asterand, Detroit, MI |
| CRC81 | Asterand, Detroit, MI |
| CRC82 | Asterand, Detroit, MI |
| CRC83 | Asterand, Detroit, MI |
| CRC84 | Asterand, Detroit, MI |
| CRC85 | Asterand, Detroit, MI |
| CRC86 | Asterand, Detroit, MI |
| CRC87 | Asterand, Detroit, MI |
| CRC88 | Asterand, Detroit, MI |
| CRC89 | Asterand, Detroit, MI |
| CRC90 | Asterand, Detroit, MI |
| CRC91 | Asterand, Detroit, MI |
| CRC92 | Asterand, Detroit, MI |
| CRC93 | Asterand, Detroit, MI |
| CRC94 | Asterand, Detroit, MI |
| CRC21 | Genomics Collaborative (Bioserve) Beltsville, MD |
| CRC22 | Genomics Collaborative (Bioserve) Beltsville, MD |
| CRC23 | Genomics Collaborative (Bioserve) Beltsville, MD |
| CRC24 | Genomics Collaborative (Bioserve) Beltsville, MD |
| CRC25 | Genomics Collaborative (Bioserve) Beltsville, MD |
| CRC26 | Genomics Collaborative (Bioserve) Beltsville, MD |

TABLE 3-continued

| ID | Source |
|---|---|
| CRC27 | Genomics Collaborative (Bioserve) Beltsville, MD |
| CRC28 | Genomics Collaborative (Bioserve) Beltsville, MD |
| CRC29 | Genomics Collaborative (Bioserve) Beltsville, MD |
| CRC30 | Genomics Collaborative (Bioserve) Beltsville, MD |
| CRC31 | Genomics Collaborative (Bioserve) Beltsville, MD |
| CRC32 | Genomics Collaborative (Bioserve) Beltsville, MD |
| CRC33 | Genomics Collaborative (Bioserve) Beltsville, MD |
| CRC34 | Genomics Collaborative (Bioserve) Beltsville, MD |
| CRC100 | Ontario Tumor Bank, Toronto, CA |
| CRC101 | Ontario Tumor Bank, Toronto, CA |
| CRC102 | Ontario Tumor Bank, Toronto, CA |
| CRC103 | Ontario Tumor Bank, Toronto, CA |
| CRC104 | Ontario Tumor Bank, Toronto, CA |
| CRC105 | Ontario Tumor Bank, Toronto, CA |
| CRC106 | Ontario Tumor Bank, Toronto, CA |
| CRC107 | Ontario Tumor Bank, Toronto, CA |
| CRC108 | Ontario Tumor Bank, Toronto, CA |
| CRC109 | Ontario Tumor Bank, Toronto, CA |
| CRC110 | Ontario Tumor Bank, Toronto, CA |
| CRC111 | Ontario Tumor Bank, Toronto, CA |
| CRC112 | Ontario Tumor Bank, Toronto, CA |
| CRC113 | Ontario Tumor Bank, Toronto, CA |
| CRC114 | Ontario Tumor Bank, Toronto, CA |
| CRC115 | Ontario Tumor Bank, Toronto, CA |
| CRC116 | Ontario Tumor Bank, Toronto, CA |
| CRC117 | Ontario Tumor Bank, Toronto, CA |
| CRC118 | Ontario Tumor Bank, Toronto, CA |
| CRC119 | Ontario Tumor Bank, Toronto, CA |
| CRC120 | Ontario Tumor Bank, Toronto, CA |
| CRC121 | Ontario Tumor Bank, Toronto, CA |
| CRC122 | Ontario Tumor Bank, Toronto, CA |
| CRC123 | Ontario Tumor Bank, Toronto, CA |
| CRC124 | Ontario Tumor Bank, Toronto, CA |
| CRC125 | Ontario Tumor Bank, Toronto, CA |
| CRC126 | Ontario Tumor Bank, Toronto, CA |
| CRC127 | Ontario Tumor Bank, Toronto, CA |
| CRC128 | Ontario Tumor Bank, Toronto, CA |
| CRC129 | Ontario Tumor Bank, Toronto, CA |
| CRC130 | Ontario Tumor Bank, Toronto, CA |
| CRC131 | Ontario Tumor Bank, Toronto, CA |
| CRC132 | Ontario Tumor Bank, Toronto, CA |
| CRC133 | Ontario Tumor Bank, Toronto, CA |
| CRC135 | Ontario Tumor Bank, Toronto, CA |
| CRC136 | Ontario Tumor Bank, Toronto, CA |
| CRC137 | Ontario Tumor Bank, Toronto, CA |
| CRC138 | Ontario Tumor Bank, Toronto, CA |
| CRC139 | Ontario Tumor Bank, Toronto, CA |
| CRC140 | Ontario Tumor Bank, Toronto, CA |
| CRC141 | Ontario Tumor Bank, Toronto, CA |
| CRC142 | Ontario Tumor Bank, Toronto, CA |
| CRC143 | Ontario Tumor Bank, Toronto, CA |
| CRC144 | Ontario Tumor Bank, Toronto, CA |
| CRC145 | Ontario Tumor Bank, Toronto, CA |
| CRC146 | Ontario Tumor Bank, Toronto, CA |
| CRC147 | Ontario Tumor Bank, Toronto, CA |
| CRC95 | Ontario Tumor Bank, Toronto, CA |
| CRC96 | Ontario Tumor Bank, Toronto, CA |
| CRC97 | Ontario Tumor Bank, Toronto, CA |
| CRC98 | Ontario Tumor Bank, Toronto, CA |
| CRC99 | Ontario Tumor Bank, Toronto, CA |
| CRC1 | ProteoGenex, Culver City, CA |
| CRC10 | ProteoGenex, Culver City, CA |
| CRC11 | ProteoGenex, Culver City, CA |
| CRC12 | ProteoGenex, Culver City, CA |
| CRC13 | ProteoGenex, Culver City, CA |
| CRC14 | ProteoGenex, Culver City, CA |
| CRC15 | ProteoGenex, Culver City, CA |
| CRC16 | ProteoGenex, Culver City, CA |
| CRC17 | ProteoGenex, Culver City, CA |
| CRC18 | ProteoGenex, Culver City, CA |
| CRC19 | ProteoGenex, Culver City, CA |
| CRC2 | ProteoGenex, Culver City, CA |
| CRC20 | ProteoGenex, Culver City, CA |
| CRC3 | ProteoGenex, Culver City, CA |
| CRC4 | ProteoGenex, Culver City, CA |
| CRC5 | ProteoGenex, Culver City, CA |
| CRC6 | ProteoGenex, Culver City, CA |
| CRC7 | ProteoGenex, Culver City, CA |
| CRC8 | ProteoGenex, Culver City, CA |
| CRC9 | ProteoGenex, Culver City, CA |

Step 3. Data quality control. We applied the data quality control procedure described in Example 1 to our CRC CGH data. A total of 43 tumor samples were found to be significantly contaminated by normal cells. We used the remaining 101 tumor samples together with the 35 cell lines in our analysis.

Step 4. Data smoothing and dimension reduction. Using the method described in Example 1, we reduced the dimensionality of the CGH data to 3575 segments and used this data as the data set (V) in our following analyses.

Figure 4:
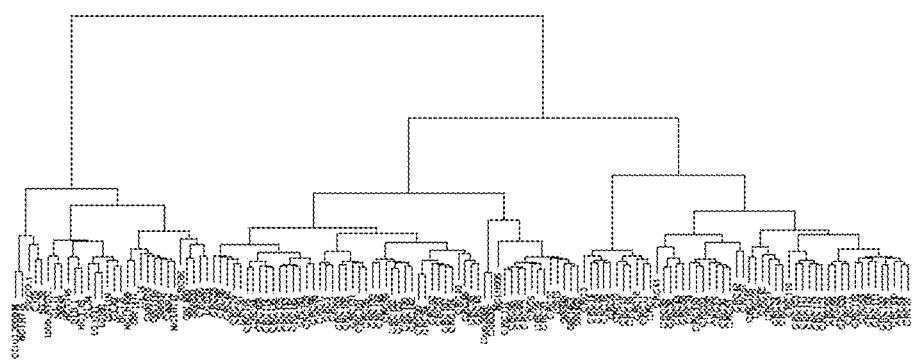
FIG. 4 shows the hierarchical clustering used to generate a dendrogram of a colorectal cancer (CRC) data set in order to derive the possible number of clusters as described in Example 4.

Step 5. Initial clustering analysis. Hierarchical clustering was used as initial analysis on our CRC data set to estimate the number of clusters. The dendrogram of the clustering is shown in FIG. 4. Visual inspection of the dendrogram suggested the existence of 3-6 major clusters in the data set.

Step 6. Classification of CRC tumors and cell lines using gNMF. The gNMF algorithm was used as described in Example 1 to classify the tumor and cell line CGH data, using cluster numbers in the range of 3-6. With each cluster number, the gNMF algorithm was run 200 times using the stop criterion developed (See, Example 1). Classification models were then derived by hierarchical clustering on 1 minus the average of correlation matrix of H.

Figure 5:
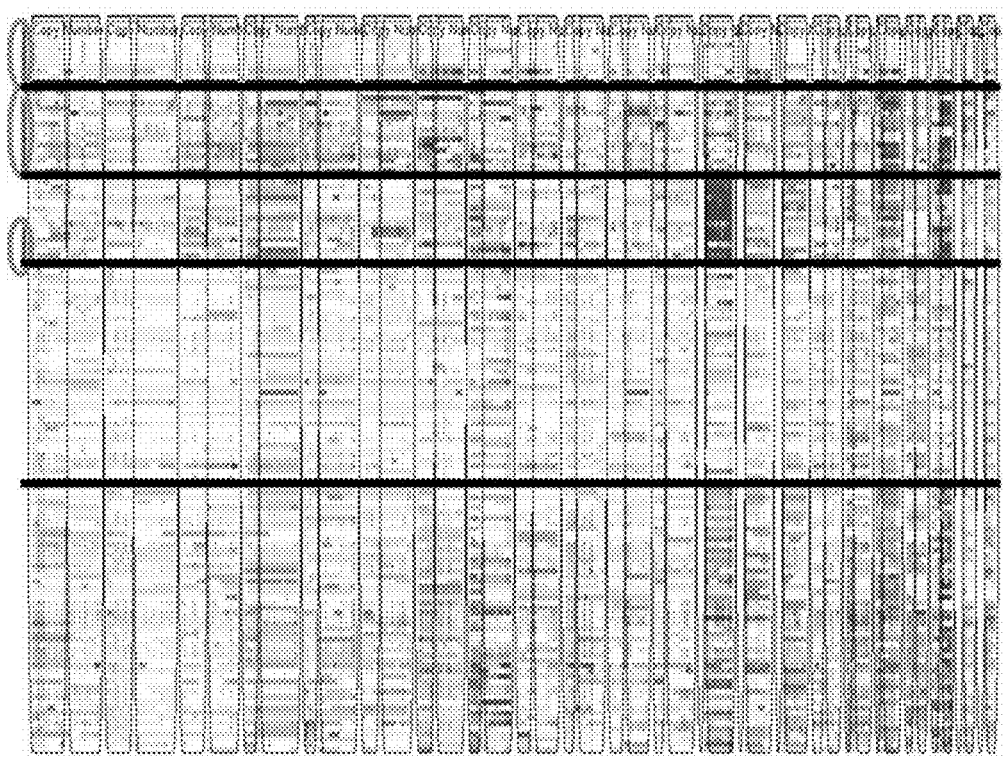
FIG. 5 shows a heatmap of CRC tumor and cell line CGH data from Example 4 classified into 5 clusters by gNMF. Each row represents a sample and each column represents a SNPs locus; red, white and blue colors indicate high, normal and low copy numbers, respectively; horizontal black lines separate different clusters; vertical spaces separate chromosomes 1 to 22; cell lines are highlighted by green circles.

Step 7. Model selection using Cophenetic correlation and BIC. We calculated the Cophenetic correlation and BIC as described in Example 1 for the gNMF models developed in step 6. The results are shown below in Table 4. In this table, r denotes the number of clusters in each model. From Table 4, we found that the model with 5 clusters had the smallest BIC, while between cluster numbers 4 and 5, the Cophenetic correlation showed the greatest decrease. Eventually, we decided that 5 clusters was the best choice for this data set. The heatmap of the gNMF output with 5 clusters is shown in FIG. 5.

TABLE 4

| r | Cophenetic correlation | BIC |
|---|---|---|
| 3 | 0.9460 | 116461 |
| 4 | 0.8786 | 93097 |
| 5 | 0.7480 | 73006 |
| 6 | 0.7610 | 105089 |

Step 8. The 10-fold test of clustering stability. We applied the 10-fold stability test described in Example 1 to the gNMF model with 5 clusters. The error rate was 16.78%. As a comparison, we also cut the hierarchical clustering dendrogram derived using the smoothed copy number data in step 5 into 3-6 clusters, and tested the stability of the clusters using the same 10-fold test. The error rates were 14.51%-18.98%.

EXAMPLE 5

Classification of Melanoma Tumors and Cell Lines

Steps 1-2. DNA extraction and hybridization and copy number determination and detection of copy number alterations. We used 30 cell lines and 109 tumor short-term cultures in this study (all cell lines are listed in Table C and all tumor CGH data are available from the Broad Institute and are described in Lin, W. M., et al., Cancer Res, 2008. 68(3): 664-73). The CGH data for melanoma tumor short-term cultures and cell line were downloaded and analyzed as described in Example 2. A total of 5616 segments with a significantly altered copy number were detected.

Step 3. Data quality control. We applied the data quality control procedure described in Example 1 to our melanoma CGH data. A total of 29 tumor samples were found to be significantly contaminated by normal cells. Therefore, we used the remaining 80 short-term culture samples together with 30 cell lines in our analysis.

Step 4. Data smoothing and dimension reduction. Using the method described in Example 1, we reduced the dimensionality of the CGH data to 4637 segments and used this data as the data set (V) in our following analyses.

Figure 6:
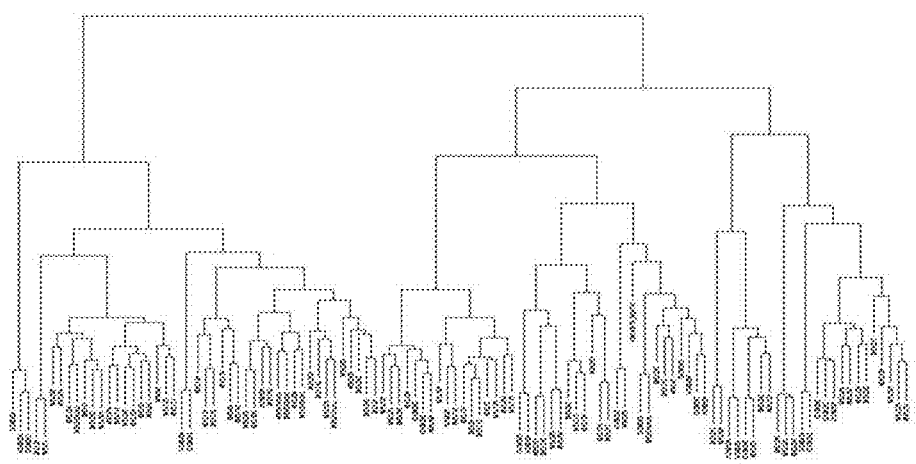
FIG. 6 shows the hierarchical clustering used to generate a dendrogram of a melanoma data set in order to derive the possible number of clusters as described in Example 5.

Step 5. Initial clustering analysis. Hierarchical clustering was used as initial analysis on our melanoma data set to estimate the number of clusters. The dendrogram of the clustering is shown as FIG. 6. Visual inspection of the dendrogram suggested the existence of 2-7 major clusters in the data set.

Step 6. Classification of melanoma tumors and cell lines using gNMF. The gNMF algorithm described in Example 2 was used to classify the tumor and cell line CGH data, using cluster numbers in the range of 2-7. With each cluster number, the gNMF algorithm was run 200 times using the stop criterion developed (See, Example 2). Classification models were then derived by hierarchical clustering on 1 minus the average of correlation matrix of H.

Figure 7:
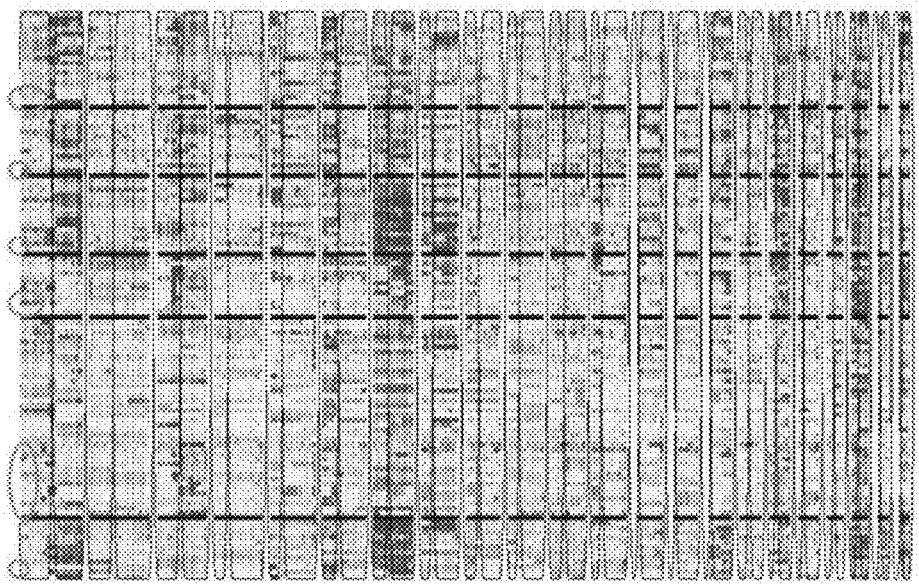
FIG. 7 shows a heatmap of melanoma tumor and cell line CGH data classified by gNMF into 6 clusters as described in Example 5. Each row represents a sample and each column represents a SNPs locus; red, white and blue colors indicate high, normal and low copy numbers, respectively; horizontal black lines separate different clusters; vertical spaces separate chromosomes 1 to 22; cell lines are highlighted by green circles.

Step 7. Model selection using BIC. We calculated the BIC as described in Example 2 for the gNMF models developed in step 6. The results are shown in Table 5. In this table, r denotes the number of clusters in each model. From Table 5, we found that the model with 6 clusters has the smallest BIC. Therefore, we decided that 6 clusters should be the best choice for this data set. The heatmap of the gNMF output with 6 clusters is shown in FIG. 7.

TABLE 5

| r | BIC |
|---|-----|
| 2 | 72202 |
| 3 | 67964 |
| 4 | 68822 |
| 5 | 61743 |
| 6 | 51893 |
| 7 | 63302 |

Step 8. The 10-fold test of clustering stability. We applied the 10-fold stability test described in Example 2 to the gNMF model with 6 clusters. The error rate was 26.42%. As a comparison, we also cut the hierarchical clustering dendrogram derived using the smoothed copy number data in step 5 into 2-7 clusters, and tested the stability of the clusters using the same 10-fold test. The error rates were 17.94%-32.14%.

EXAMPLE 6

Assembly of Cell Line Panels for Use in Pre-Clinical Testing

Using the methods described above in Examples 1-5, we classified our non-small cell lung carcinoma, colorectal cancer and melanoma cell line and tumor CGH data into 4, 5 and 6 clusters respectively (See, Tables 4-6 below). From each of these clusters at least one cell line was selected to construct a panel representative of all genomic subgroups of the cancer type under consideration.

The assembled panels of cell lines can be used as pre-clinical models for oncology drug testing for each specific subcategory of cancer. For example, for the 4 clusters of NSCLC shown below in Table 6, the panel can include: HCC827 from cluster A, NCI-H2405 from cluster B and A549 from cluster C. There were no cancer cell lines representing cluster D.

For the 5 clusters of CRC shown below in Table 7, the panel can include: HCT-8 from cluster A, Caco-2 from cluster B, and Colo 320DM from cluster C. There were no cancer cell lines representing cluster D and cluster E.

For the 6 clusters of melanoma shown below in Table 8, a panel can include: SKMEL119 from cluster A, WM3248 from cluster B, 1205LU from cluster C, 451LU from cluster D, WM3211 from cluster E, and MALME3M from cluster F.

TABLE 6

| Clusters | Number of tumors | Cancer Cell Lines |
|----------|------------------|-------------------|
| Cluster A | 19 | HCC827, NCI-H1437, NCI-H1563, NCI-H1568, NCI-H1623, NCI-H1651, NCI-H1693, NCI-H1755, NCI-H1793, NCI-H1838, NCI-H1944, NCI-H1975, NCI-H1993, NCI-H2023, NCI-H2073, NCI-H2085, NCI-H2087, NCI-H2122, NCI-H2126, NCI-H2228, NCI-H2291, NCI-H23, NCI-H2342, NCI-H2347, NCI-H647, NCI-H920, NCI-H969, CLS-54, LX-289, SK-LU-1, H2882, Calu-6, H358, H460 |
| Cluster B | 60 | NCI-H2405, NCI-H522, SK-MES-1, H157, H1819, H2009, H2887, HCC1171, HCC1359, HCC15, HCC193, HCC366, HCC461, HCC515, HCC78, HOP-62, HOP-92, NCI-H266 |
| Cluster C | 42 | A549, Calu-3, NCI-H1734, NCI-H838, HCC95 |
| Cluster D | 124 | |

TABLE 7

| Clusters | Number of tumors | Cancer Cell Lines |
|----------|------------------|-------------------|
| Cluster A | 0 | HCT-8, LS 174T, SK-CO-1, SW48, DLD-1, HCT-15, HCT116, LoVo, CL-34, CL-40, C170, LS180 |
| Cluster B | 2 | Caco-2, LS1034, LS411N, LS513, NCI-H498, NCI-H747, SW1116, SW1417, SW837, HT-29, SW620, CL-11, CL-14, Colo-678, SW-480 |
| Cluster C | 8 | Colo 320DM, NCI-H508, NCI-H716, SW1463, SW403, SW948, Colo 205, Colo-206F |
| Cluster D | 40 | |
| Cluster E | 51 | |

TABLE 8

| Clusters | Number of tumors | Cancer Cell Lines |
|---|---|---|
| Cluster A | 15 | SKMEL119, HS944, WM1366, WM88 |
| Cluster B | 12 | WM3248 |
| Cluster C | 14 | 1205LU |
| Cluster D | 4 | 451LU, SKMEL19, SKMEL28, SKMEL30, SKMEL63, WM35, WM983, WM983C |
| Cluster E | 25 | WM3211, M14, MEWO, SKMEL2, SKMEL5, UACC257, UACC62, WM122, WM13662, WM239A, WM32112, WM32482, WM793B, 501MEL |
| Cluster F | 10 | MALME3M, WM882 |

EXAMPLE 7

Validation of the Genomic Clustering Results Using Outcome-Annotated Tumor Samples To determine whether the NSCLC genomic clusters identified have biologically meaningful differences, two sets of tumor samples were used with disease outcome annotation. Two outcome parameters were used, time to recurrence (TTR) and overall survival (OS).

Figure 8:
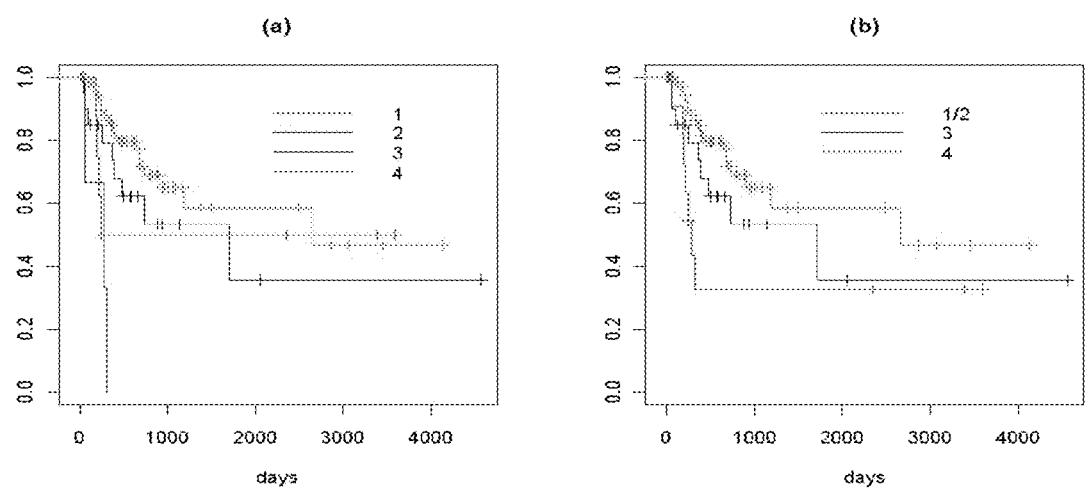
FIG. 8 shows Kaplan-Meier curve of the time to recurrence for clinically annotated samples in the four NSCLC clusters: (a) four clusters considered separately; and (b) clusters 1 and 2 combined.

Among the 245 NSCLC tumor samples used in NSCLC classification (See, Example 3, Table 1), disease outcome information (overall survival and time to recurrence) was available for 111 samples collected at Rush University Medical Center, Chicago, Ill. The numbers of outcome-annotated samples in clusters 1, 2, 3, and 4 were 9, 3, 21 and 78, respectively. A logrank test comparing their TTRs showed a significant P-value of 0.0006. Since there were only three samples in cluster 2, an effort was made to combine samples in cluster 1 and cluster 2 together. The combined samples had significantly lower TTR than the other 2 clusters with P-value of 0.0397. The Kaplan-Meier curves are shown in FIG. 8.

To further validate the unsupervised clustering algorithm for cancer classification based on copy number alterations, and the cell line models selected to present different subgroups of cancer patients, an additional study using 71 NSCLC tumor samples (Table 9, below) was used with associated outcome information.

TABLE 9

Validation samples and sources

| Sample ID | Source |
|---|---|
| SML-007 | Samsung Medical Center, Seoul, Korea (Dr. Kim) |
| SML-008 | Samsung Medical Center, Seoul, Korea (Dr. Kim) |
| SML-012 | Samsung Medical Center, Seoul, Korea (Dr. Kim) |
| SML-013 | Samsung Medical Center, Seoul, Korea (Dr. Kim) |
| SML-014 | Samsung Medical Center, Seoul, Korea (Dr. Kim) |
| SML-019 | Samsung Medical Center, Seoul, Korea (Dr. Kim) |
| SML-047 | Samsung Medical Center, Seoul, Korea (Dr. Kim) |
| SML-048 | Samsung Medical Center, Seoul, Korea (Dr. Kim) |
| SML-053 | Samsung Medical Center, Seoul, Korea (Dr. Kim) |
| SML-070 | Samsung Medical Center, Seoul, Korea (Dr. Kim) |
| SML-071 | Samsung Medical Center, Seoul, Korea (Dr. Kim) |
| SML-083 | Samsung Medical Center, Seoul, Korea (Dr. Kim) |
| SML-086 | Samsung Medical Center, Seoul, Korea (Dr. Kim) |
| SML-093 | Samsung Medical Center, Seoul, Korea (Dr. Kim) |
| SML-094 | Samsung Medical Center, Seoul, Korea (Dr. Kim) |
| SML-095 | Samsung Medical Center, Seoul, Korea (Dr. Kim) |
| SML-096 | Samsung Medical Center, Seoul, Korea (Dr. Kim) |
| SML-103 | Samsung Medical Center, Seoul, Korea (Dr. Kim) |
| SML-107 | Samsung Medical Center, Seoul, Korea (Dr. Kim) |
| SML-110 | Samsung Medical Center, Seoul, Korea (Dr. Kim) |
| SML-111 | Samsung Medical Center, Seoul, Korea (Dr. Kim) |
| SML-118 | Samsung Medical Center, Seoul, Korea (Dr. Kim) |
| SML-119 | Samsung Medical Center, Seoul, Korea (Dr. Kim) |
| SML-120 | Samsung Medical Center, Seoul, Korea (Dr. Kim) |
| SML-122 | Samsung Medical Center, Seoul, Korea (Dr. Kim) |
| SML-123 | Samsung Medical Center, Seoul, Korea (Dr. Kim) |
| SML-137 | Samsung Medical Center, Seoul, Korea (Dr. Kim) |
| SML-138 | Samsung Medical Center, Seoul, Korea (Dr. Kim) |
| SML-141 | Samsung Medical Center, Seoul, Korea (Dr. Kim) |
| SML-142 | Samsung Medical Center, Seoul, Korea (Dr. Kim) |
| SML-143 | Samsung Medical Center, Seoul, Korea (Dr. Kim) |
| SML-144 | Samsung Medical Center, Seoul, Korea (Dr. Kim) |
| SML-176 | Samsung Medical Center, Seoul, Korea (Dr. Kim) |
| SML-192 | Samsung Medical Center, Seoul, Korea (Dr. Kim) |
| SML-198 | Samsung Medical Center, Seoul, Korea (Dr. Kim) |
| SML-209 | Samsung Medical Center, Seoul, Korea (Dr. Kim) |
| SML-231 | Samsung Medical Center, Seoul, Korea (Dr. Kim) |
| SML-232 | Samsung Medical Center, Seoul, Korea (Dr. Kim) |
| SML-237 | Samsung Medical Center, Seoul, Korea (Dr. Kim) |
| SML-239 | Samsung Medical Center, Seoul, Korea (Dr. Kim) |
| SML-244 | Samsung Medical Center, Seoul, Korea (Dr. Kim) |
| SML-055 | Samsung Medical Center, Seoul, Korea (Dr. Kim) |
| SML-088 | Samsung Medical Center, Seoul, Korea (Dr. Kim) |
| SML-018 | Samsung Medical Center, Seoul, Korea (Dr. Kim) |
| SML-021 | Samsung Medical Center, Seoul, Korea (Dr. Kim) |
| SML-024 | Samsung Medical Center, Seoul, Korea (Dr. Kim) |
| SML-028 | Samsung Medical Center, Seoul, Korea (Dr. Kim) |

TABLE 9-continued

Validation samples and sources

| Sample ID | Source |
| --- | --- |
| SML-029 | Samsung Medical Center, Seoul, Korea (Dr. Kim) |
| SML-030 | Samsung Medical Center, Seoul, Korea (Dr. Kim) |
| SML-031 | Samsung Medical Center, Seoul, Korea (Dr. Kim) |
| SML-033 | Samsung Medical Center, Seoul, Korea (Dr. Kim) |
| SML-035 | Samsung Medical Center, Seoul, Korea (Dr. Kim) |
| SML-037 | Samsung Medical Center, Seoul, Korea (Dr. Kim) |
| SML-039 | Samsung Medical Center, Seoul, Korea (Dr. Kim) |
| SML-040 | Samsung Medical Center, Seoul, Korea (Dr. Kim) |
| SML-041 | Samsung Medical Center, Seoul, Korea (Dr. Kim) |
| SML-044 | Samsung Medical Center, Seoul, Korea (Dr. Kim) |
| SML-062 | Samsung Medical Center, Seoul, Korea (Dr. Kim) |
| SML-064 | Samsung Medical Center, Seoul, Korea (Dr. Kim) |
| SML-067 | Samsung Medical Center, Seoul, Korea (Dr. Kim) |
| SML-068 | Samsung Medical Center, Seoul, Korea (Dr. Kim) |
| SML-079 | Samsung Medical Center, Seoul, Korea (Dr. Kim) |
| SML-080 | Samsung Medical Center, Seoul, Korea (Dr. Kim) |
| SML-091 | Samsung Medical Center, Seoul, Korea (Dr. Kim) |
| SML-092 | Samsung Medical Center, Seoul, Korea (Dr. Kim) |
| SML-099 | Samsung Medical Center, Seoul, Korea (Dr. Kim) |
| SML-100 | Samsung Medical Center, Seoul, Korea (Dr. Kim) |
| SML-105 | Samsung Medical Center, Seoul, Korea (Dr. Kim) |
| SML-116 | Samsung Medical Center, Seoul, Korea (Dr. Kim) |
| SML-147 | Samsung Medical Center, Seoul, Korea (Dr. Kim) |
| SML-203 | Samsung Medical Center, Seoul, Korea (Dr. Kim) |

The samples were processed, DNA were extracted, amplified and hybridized to Affymetrix SNP 6.0 arrays following Affymetrix experimental protocols (See, Examples 1 and 3). Copy number of these tumors was calculated by comparing to HapMap set of 270 normal controls. The copy number was segmented using Partek software 6.09.0310 (See, Example 2).

To assign the validation samples to the four NSCLC clusters, Pearson correlation coefficients of the outcome-annotated tumor samples were calculated for each of the representative cell lines of the first three clusters (See Examples 1-3). Since the $4^{th}$ cluster did not have representative cell line, all tumor samples in the $4^{th}$ cluster were used as its representatives and calculated their Pearson correlation coefficient to the validation samples. The validation samples were then assigned to the cluster that contained the representative cell line or tumor that has the highest correlation coefficient with the validation sample. Finally, the differences in TTR and OS of the validation samples assigned into different clusters were compared using a logrank test and plotted their Kaplan-Meier curves (See, Examples 1-3).

Figure 9:
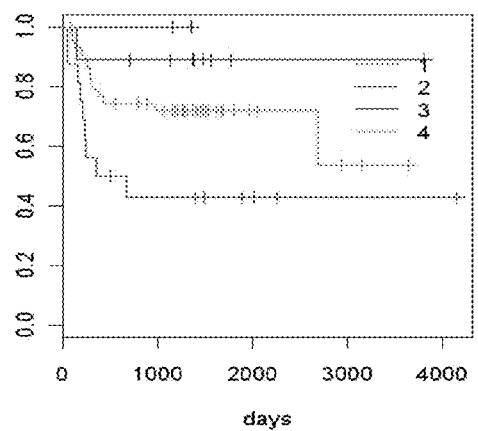
FIG. 9 shows Kaplan-Meier curve of the TTR for the validation samples assigned into the four clusters: (a) four clusters considered separately; and (b) cluster 1 compared with the remaining three clusters.
Figure 9:
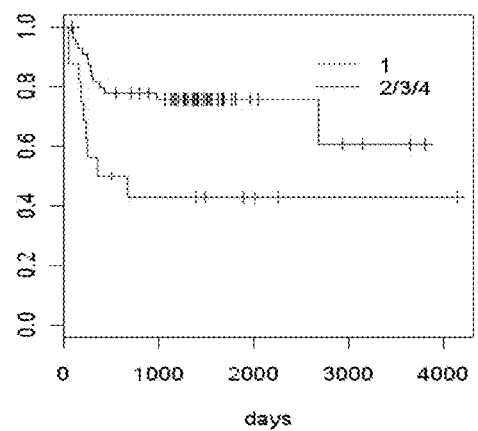

The difference in TTR between the four clusters is significant with a P-value of 0.0454 for the validation samples. Furthermore, the Kaplan-Meier curve showed a significantly lower TTR for samples in cluster 1 relative to the other clusters (See, FIG. 9). If samples in clusters 2, 3, and 4 are combined and compared to the samples in cluster 1, the P-value is 0.0094.

Figure 10:
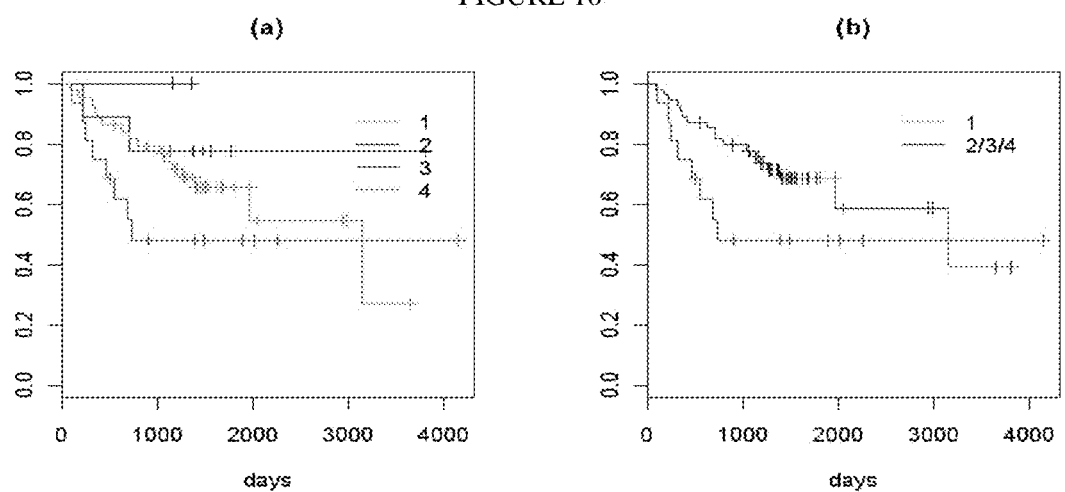
FIG. 10 shows Kaplan-Meier curve of the Overall Survival between the validation samples assigned into the four clusters: (a) four clusters considered separately; and (b) cluster 1 compared with the remaining three clusters.

The difference in OS between the 4 clusters was not significant (P-value=0.25) for the validation samples, but the Kaplan-Meier curve showed a trend of lower OS for samples in cluster 1 relative to the other clusters (See, FIG. 10). If samples in clusters 2, 3, and 4 are combined and compared to samples in cluster 1, the P-value is marginally significant (P-value=0.116).

Figure 11:
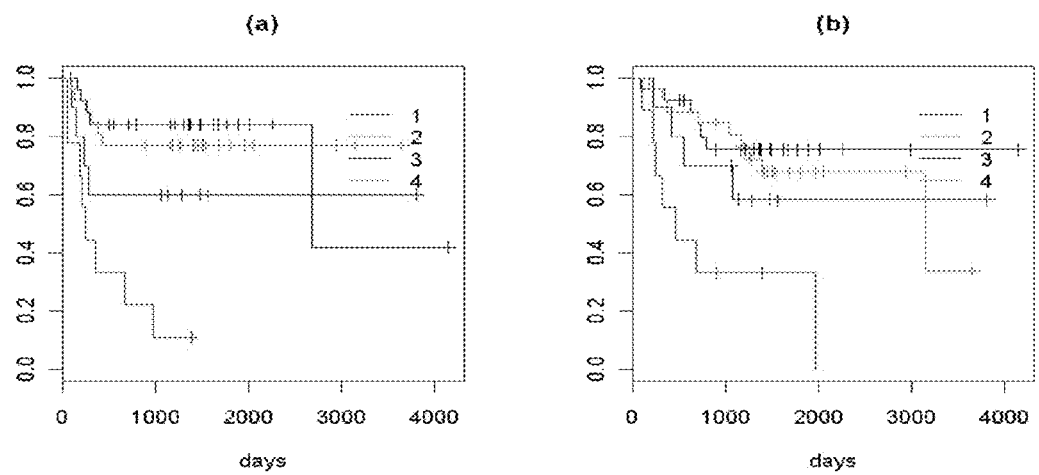
FIG. 11 shows Kaplan-Meier curve of the TTR and OS between the validation samples assigned into the four clusters using all existing tumor and cell lines to represent the clusters: (a) TTR; and (b) OS.

Alternatively, all tumors and cell lines in our already defined clusters was used to represent the clusters and assigned the validation samples to the four clusters by the highest Pearson correlation coefficient between the validation samples and the existing samples. In this analysis, both TTR and OS showed significant differences between the four clusters with P-values of 4.7E-5 and 0.0024, respectively. Samples assigned to cluster 1 had a significantly lower TTR and OS than samples assigned to other clusters (See, FIG. 11).

To conclude, outcome-annotated samples were used in the data set as well as independent samples to determine whether the NSCLC genomic clusters identified have biologically meaningful differences. The results show that the clusters differ significantly in time to recurrence and overall survival of patients, indicating that the genomic classification correlates with differences in the disease course, and the cell lines representing different clusters can be used as models to predict different clinical outcomes.

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for identifying pharmaceutical compounds for the treatment of particular solid tumor cells, the method comprising the steps of:

(i) selecting at least one solid tumor cell line from each subgroups from a panel of solid tumor cells classified according to genomic subgroups, wherein the panel is assembled from a method comprising:

(a) obtaining a plurality of m samples comprising at least one tumor or cancer cell line;

(b) acquiring a first data set comprising copy number alteration information from at least one locus from each chromosome from each sample obtained in step (a);

(c) identifying in the first data set, copy number alteration information obtained from samples contaminated by normal cells and eliminating the contaminated samples from the first data set, wherein the identifying and eliminating comprises:

(1) applying a machine learning algorithm tuned to parameters that represent the differences between tumor and normal samples to the data;

(2) assigning a probability score for normal cell contamination to each sample as determined by the machine learning algorithm;

(3) eliminating data from the first data set for each sample scoring 50% or greater probability of being contaminated by normal cells;

(d) estimating a range of a number of subgroups, r, in the data set by applying an unsupervised clustering algorithm using Pearson linear dissimilarity algorithm to the data set to generate a dendrogram;

(e) assigning each sample in the data set to at least one subgroup using a modified genomic non-negative matrix factorization (gNMF) algorithm with each one of the r values estimated in step (d), wherein the modified gNMF algorithm comprises:

(1) calculating divergence of the gNMF algorithm after every 100 steps of one run of multiplicative updating of the gNMF algorithm using the formula (1):

$$D(V\|WH) = \sum_{i=1}^{n}\sum_{j=1}^{m}\left(V_{ij}\log\frac{V_{ij}}{(WH)_{ij}} - V_{ij} + (WH)_{ij}\right) \quad (1)$$

wherein the $V_{ij}$ is the $i^{th}$ row and $j^{th}$ column of matrix V, $(WH)_{ij}$ is the $i^{th}$ row and $j^{th}$ column of matrix (W*H), i runs from 1 to n and n is the number of DNA segments in the data set, and j runs from 1 to m and m is the number of samples in the data set;

(2) stopping the gNMF algorithm if the divergence calculated in step (e)(1) does not decrease by more than about 0.001% when compared to the divergence calculated for the previous 100 steps of multiplicative updating of the gNMF algorithm;

(3) repeating the gNMF algorithm for a selected number of runs, each with a random start point, and calculating a Pearson correlation coefficient matrix of H for each run of the gNMF algorithm using the formula (2):

$$C_{i,j} = \rho(H_{\cdot,i}, H_{\cdot,j}) = \frac{\frac{1}{r-1}\sum_{k}(H_{k,i} - \overline{H_{\cdot,i}})(H_{k,j} - \overline{H_{\cdot,j}})}{s_{H_{\cdot,i}}s_{H_{\cdot,j}}} \quad (2)$$

wherein C is the correlation matrix, $C_{ij}$ is the $i^{th}$ row and $j^{th}$ column in the matrix C, $H_{\cdot,i}$ and $H_{\cdot,j}$ are the $i^{th}$ and $j^{th}$ column vector in matrix H, $\rho(H_{\cdot,i}, H_{\cdot,j})$ is the Pearson correlation coefficient between $H_{\cdot,i}$ and $H_{\cdot,j}$, i and j run from 1 to m and m is the number of samples in the data set, k runs from 1 to r and r is the number of subgroups from step (d);

(4) averaging the Pearson correlation coefficient matrices for each run of the gNMF algorithm obtained from step (e)(3) to arrive at an average correlation matrix;

(5) assigning samples in the data set into r subgroups by applying an unsupervised clustering algorithm using the identity matrix minus the average correlation matrix determined in step (e)(4) and cutting the dendrogram into r subgroups;

(6) repeating steps (1)-(5) with a different value of r determined in step (d);

(f) applying a Cophenetic correlation, Bayesian Information Criterion, or a combination thereof to provide a final number of subgroups from the data set, wherein each final subgroup defines a genomic subgroup for each tumor or cancer cell line sample; and (g) evaluating the stability of the final number of subgroups selected in step (f) using a ten-fold stability test;

(h) selecting at least one solid tumor cell from each subgroup selected in step (f) and assembling into panels defined according to genomic subgroups;

(ii) contacting the at least one solid tumor cell from each subgroup with the pharmaceutical compound;

(iii) assaying the efficacy of the pharmaceutical compound to treat the at least one solid tumor cell from each subgroup; and (iv) classifying the pharmaceutical compound according to the determined efficacy of the pharmaceutical compound to treat the at least one solid tumor cell from each subgroup, wherein treating the at least one solid tumor cell from one subgroup, but not another, indicates specificity of the pharmaceutical compound to treat solid tumor cells of that subgroup.

2. The method of claim 1, wherein the unsupervised clustering algorithm is a hierarchical clustering.

3. The method of claim 1, wherein Cophenetic correlation is used to provide a final number of subgroups from the data set.

4. The method of claim 1, wherein Bayesian Information Criterion is used to provide a final number of subgroups from the data set.

5. The method of claim 1, wherein Cophenetic correlation and Bayesian Information Criterion are used to provide a final number of subgroups from the data set.

* * * * *